(12) United States Patent
Kyle et al.

(10) Patent No.: US 8,697,941 B2
(45) Date of Patent: Apr. 15, 2014

(54) MOLECULAR MARKERS LINKED TO PPO INHIBITOR TOLERANCE IN SOYBEANS

(75) Inventors: Donald Kyle, Princeton, IL (US); Mark D. Vogt, Ankeny, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 926 days.

(21) Appl. No.: 12/506,498

(22) Filed: Jul. 21, 2009

(65) Prior Publication Data

US 2010/0024080 A1 Jan. 28, 2010

Related U.S. Application Data

(60) Provisional application No. 61/083,038, filed on Jul. 23, 2008.

(51) Int. Cl.
A01H 1/04 (2006.01)

(52) U.S. Cl.
USPC .......................................... 800/267; 800/312

(58) Field of Classification Search
None
See application file for complete search history.

(56) References Cited

U.S. PATENT DOCUMENTS

| | | | |
|---|---|---|---|
| 4,761,373 | A | 8/1988 | Anderson et al. |
| 5,013,659 | A | 5/1991 | Bedbrook et al. |
| 5,141,870 | A | 8/1992 | Bedbrook et al. |
| 5,304,732 | A | 4/1994 | Anderson et al. |
| 5,331,107 | A | 7/1994 | Anderson et al. |
| 5,378,824 | A | 1/1995 | Bedbrook et al. |
| 5,489,520 | A | 2/1996 | Adams et al. |
| 5,550,318 | A | 8/1996 | Adams et al. |
| 5,561,236 | A | 10/1996 | Leemans et al. |
| 5,605,011 | A | 2/1997 | Bedbrook et al. |
| 5,646,024 | A | 7/1997 | Leemans et al. |
| 5,648,477 | A | 7/1997 | Leemans et al. |
| 5,731,180 | A | 3/1998 | Dietrich |
| 5,767,361 | A | 6/1998 | Dietrich |
| 5,767,373 | A | 6/1998 | Ward et al. |
| 5,874,265 | A | 2/1999 | Adams et al. |
| 5,879,903 | A | 3/1999 | Strauch |
| 5,919,675 | A | 7/1999 | Adams et al. |
| 5,928,937 | A | 7/1999 | Kakefuda et al. |
| 5,969,213 | A | 10/1999 | Adams et al. |
| 6,069,115 | A | 5/2000 | Pallett et al. |
| 6,177,616 | B1 | 1/2001 | Bartsch et al. |
| 6,245,968 | B1 | 6/2001 | Boudec et al. |
| 6,268,549 | B1 | 7/2001 | Sailland et al. |
| 6,282,837 | B1 | 9/2001 | Ward et al. |
| 6,288,306 | B1 | 9/2001 | Ward et al. |
| 6,307,129 | B1 | 10/2001 | Ward et al. |

FOREIGN PATENT DOCUMENTS

| | | |
|---|---|---|
| WO | WO 96/33270 | 10/1996 |
| WO | WO 99/23886 | 5/1999 |
| WO | WO 01/12825 | 2/2001 |
| WO | WO 2005/107437 | 11/2005 |
| WO | 2006/017840 A | 2/2006 |
| WO | WO 2006/017840 | 2/2006 |
| WO | WO 2010/011803 | 1/2010 |

OTHER PUBLICATIONS

Hulting. A.G., et al., "Soybean (*Glycine max* (L.) Merr.) cultivar tolerance to sulfentrazone", Crop Protection, 20 (8):679-683 (2001). XP002547823.
Dayan, F.E. et al.; "Soybean (*Glycine max*) cultivar differences in response to sulfentrazon", Weed Science, Weed Science Society of America, Champaign, IL, US, 45(5):634-641 (1997). XP009123163.
Li, Z., et al., "Using electrolyte leakage to detect soybean (*Glycine max*) cultivars sensitive to sulferitrazone", Weed Technology, Champaign, IL, US, 14(4):699-704 (2000). XP009123189.
Li, Zhaohu et al., "Physiological basis for the differential tolerance of *Glycine max* to sulfentrazone during seed germination", Weed Science, 48:281-285, 2000.
Swantek, J.M., et al., "Evaluation of soybean injury from sulfentrazone and inheritance of tolerance", Weed Science, Weed Science Society of America, Champaign, IL., US, 46(2)271-277 (1988). XP009123188.
Taylor-Lovell, Sarah et al., "Phytotoxic Response and Yield of Soybean (*Glycine max*) Varieties Treated with Sulfentrazone or Flumioxazin" Weed Technology, 2001. vol. 15:95-102.
PCT International Search Report, Pioneer Hi-Bred International, Inc., PCT/US2009/051483, mailed Oct. 13, 2009, 5 pages.
Shoemaker and Olsen, ((1993) Molecular Linkage Map of Soybean (*Glycine max* L. Merr.). p. 6.131-6.138. In S.J. O'Brien (ed.) Genetic Maps: Locus Maps of Complex Genomes . . . .
Shoemaker R.C., 1994 RFLP Map of Soybean. p. 299-309 in R.L. Phlllips and I.K. Vasil (ed.) DNA-based markers in plants. Kluwer Academic Press Dordrecht, the Netherlands.
Choi, et al., "A soybean transcript map: Gene distribution, haplotype and single nucleotide polymorphism analysis", Genetics, vol. 176, pp. 685-696 (2007).
Cregan, P.B., et al., "An integrated genetic linkage map of the soybean genome", Crop Science, vol. 39, pp. 1464-1490 (1990).
Dayan et al., "Soybean (*Glycine max*) cultivar differences in response to sulfentrazone", Weed Science, vol. 45, pp. 634-641 (1997).
Henikoff, et al., "Amino acid substitution matrices from protein blocks" Proc Natl. Acad. Sci. USA, vol. 89, pp. 10915-10919 (1992).
Herman, et al., "A Three -component Dicamba O-Demethylase from *Pseudomonas maltophilia*, Strain DI-6: Gene Isolation . . . ", J. Biol. Chem., vol. 280, pp. 24759-24767 (2005).
Hulting, et al., "Soybean (*Glycine max* (L.) Merr.) cultivar tolerance to sulfentrazone", Science Direct, vol. 20, pp. 679-683 (2001).
Li, Z., et al., "Physiological basis for the differential tolerance of *Glycine max* to sulfentrazone during seed germination", Weed Science, vol. 48, pp. 281-285 (2000).
Li, Z., et al., "Using electrolyte leakage to detect soybean (*Glycine max*) cultivars sensitive to sulfentrazone", Weed Technology, vol. 14, pp. 699-704 (2000).

(Continued)

Primary Examiner — Shubo (Joe) Zhou
Assistant Examiner — Keith Robinson

(57) ABSTRACT

This invention relates generally to the detection of genetic differences among soybeans. More particularly, the invention relates to soybean quantitative trait loci (QTL) for tolerance to protoporphyrinogen oxidase inhibitors, to soybean plants possessing these QTLs, which map to a novel chromosomal region, and to genetic markers that are indicative of phenotypes associated with protoporphyrinogen oxidase inhibitor tolerance. Methods and compositions for use of these markers in genotyping of soybean and selection are also disclosed.

10 Claims, 6 Drawing Sheets

(56) References Cited

OTHER PUBLICATIONS

Needleman, et al., "A general method applicable to the search for similarities in the amino acid sequence of two proteins", J. Mol. Biol., vol. 48, pp. 443-453 (1970).

Retzinger, et al., "Classification of herbicides by site of action for weed resistance management strategies", Weed Technology, vol. 11, pp. 383-393 (1997).

Swantek: J.M., et al., "Evaluation of soybean injury from sulfentrazone and inheritance of tolerance", Weed Science, vol. 46, p. 271-277 (1998).

Taylor-Lovell, et al., "Phytoxic response and yield of soybean (*Glycine max*) varieties treated with sulfentrazone or flumioxazin", Weed Technology, vol. 15, pp. 95-102 (2001).

International Search Report in PCT/US2009/051483, mailed Oct. 13, 2009.

Copending U.S. Appl. No. 12/694,255, filed Jan. 26, 2010.

Copending U.S. Appl. No. 13/013,332, filed Jan. 25, 2011.

Copending U.S. Appl. No. 13/013,139, filed Jan. 25, 2011.

| Marker | Linkage Group | Position | Type |
|---|---|---|---|
| SATT495 | L | 0.00 | SSR |
| SATT723 | L | 0.44 | SSR |
| Sat_408 | L | 1.00 | SSR |
| Sat_301 | L | 10.31 | SSR |
| SATT446 | L | 11.13 | SSR |
| P10649C-3 | L | 12.5 | ASH |
| SATT232 | L | 12.55 | SSR |
| SATT182 | L | 13.90 | SSR |
| SATT238 | L | 19.41 | SSR |
| Sat_071 | L | 20.04 | SSR |
| SATT388 | L | 21.61 | SSR |
| SATT497 | L | 26.06 | SSR |
| SATT313 | L | 27.35 | SSR |
| SATT143 | L | 28.16 | SSR |
| Sat_397 | L | 28.26 | SSR |
| SATT418 | L | 28.57 | SSR |
| Sat_134 | L | 28.66 | SSR |
| SATT652 | L | 28.67 | SSR |
| SATT711 | L | 28.67 | SSR |
| Sat_187 | L | 28.68 | SSR |
| Sat_195 | L | 28.68 | SSR |
| Sat_388 | L | 28.71 | SSR |
| SATT694 | L | 28.71 | SSR |
| SATT398 | L | 28.90 | SSR |
| Sat_191 | L | 29.19 | SSR |
| Sat_405 | L | 29.40 | SSR |
| Sat_320 | L | 29.74 | SSR |
| SATT523 | L | 30.18 | SSR |
| SATT278 | L | 30.34 | SSR |
| SATT613 | L | 32.64 | SSR |

*FIG. 1A*

| Linked Markers | | | | | |
|---|---|---|---|---|---|
| SATT495 | SATT723 | Sat_408 | A169_1 | EV2_1 | Sle3_4s |
| BLT010_2 | BLT007_1 | SATT232 | Sat_301 | SATT446 | SATT182 |
| R176_1 | JUBC090 | SATT238 | Sat_071 | BLT039_1 | Bng071_1 |
| SATT388 | A264_1 | RGA_7 | RGA7 | SATT523 | Sat_134 |
| LbA | i8_2 | A450_2 | A106_1 | Sat_405 | SATT143 |
| B124_2 | A459_1 | SATT398 | SATT694 | Sat_195 | Sat_388 |
| SATT652 | SATT711 | Sat_187 | SATT418 | SATT278 | Sat_397 |
| Sat_191 | Sat_320 | O109_1 | A204_2 | SATT497 | G214_17 |
| SATT313 | B164_1 | G214_16 | SATT613 | A023_1 | SATT284 |
| AW508247 | SATT462 | L050_7 | E014_1 | A071_5 | B046_1 |
| L1 | B162_2 | | | | |

*FIG. 1B*

| Marker | Linkage Group | Position | Type |
|---|---|---|---|
| Sat_379 | N | 2.70 | SSR |
| SCT_195 | N | 4.63 | SSR |
| SATT631 | N | 20.31 | SSR |
| SATT159 | N | 21.76 | SSR |
| SATT009 | N | 22.42 | SSR |
| SATT641 | N | 23.32 | SSR |
| Sat_186 | N | 23.91 | SSR |
| SATT152 | N | 24.79 | SSR |
| S60167-TB | N | 26.00 | SSR |
| SATT530 | N | 27.41 | SSR |
| SATT675 | N | 28.92 | SSR |
| SATT683 | N | 28.96 | SSR |
| SATT624 | N | 29.55 | SSR |
| SATT393 | N | 29.64 | SSR |
| SATT125 | N | 30.30 | SSR |
| SATT485 | N | 30.30 | SSR |
| SATT584 | N | 30.64 | SSR |
| Sat_166 | N | 31.09 | SSR |
| Sat_084 | N | 31.36 | SSR |
| Sat_275 | N | 33.84 | SSR |
| Sat_208 | N | 35.48 | SSR |
| Sat_280 | N | 36.82 | SSR |
| SATT080 | N | 38.56 | SSR |
| Sat_266 | N | 40.02 | SSR |
| SATT387 | N | 45.03 | SSR |

*FIG. 2A*

| Linked Markers | | | | |
|---|---|---|---|---|
| SCT_195 | Sat_379 | A071_10 | A071_3 | A071_4 |
| A071_6 | AC_telo | Rps7 | R022_1 | L050_12 |
| SATT152 | OP_N03 | BLT004_1 | SATT631 | SATT159 |
| SATT009 | SATT641 | RGA6a | Sat_186 | A071_2 |
| K418_1 | Rps1 | K395_2 | OPAC12b | SATT530 |
| gc34_2 | SATT683 | SATT675 | A280_1 | SATT624 |
| A426_2 | Sle_003 | i4_2 | Sat_084 | SATT393 |
| SATT584 | SATT485 | Sat_166 | Sat_208 | BLT049_1 |
| Bng095_2 | OP_F13 | SATT125 | Sat_275 | Sle2_3 |
| Mng456_1 | RGA6b | OP_U09b | mO128_1 | Sat_280 |
| SATT080 | Sat_266 | L103_1 | B162_1 | peG488_2 |
| SATT387 | Rpg4 | Sat_236 | Sat_033 | |

*FIG. 2B*

| Marker Name | Left Primer Sequence | Right Primer Sequence | Pigtail |
|---|---|---|---|
| S60167-TB LG-N | TTATTGAGGTGGGCAAGGTGTG (SEQ ID NO. 1) | CATGAACGTCTGGTGGTTGAACA (SEQ ID NO: 2) | GTTTCTT |
| SATT523 LG-L | GCGATTCTTCCTTGAAGAATTTTCTG (SEQ ID NO. 3) | GGGCTTTTCGGCTGTTATTTTAACT (SEQ ID NO. 4) | GTTTCTT |

FIG. 3

| Marker Name | PCR Primers | Allele Probes |
|---|---|---|
| P10649C-3 LG-L | Primer Seq 1 (SEQ ID NO. 5): GAGGGCTATGTTTCTTCTCCAGATGTGAG<br>Primer Seq 2 (SEQ ID NO. 6): AAGGTCGGCTTGGTGGTTAAAGGCAG | Allele 1 Probe (SEQ ID NO. 7): TCATcTgTGATAA<br>Allele 2 Probe (SEQ ID NO. 8): TCATgTgTGATAA<br>Allele 3 Probe (SEQ ID NO. 9): TCATcTcTGATAA |
| S00224-1 LG-L | Primer Seq 1 (F) (SEQ ID NO. 10): CTGGACCTACCCGGGATGAAAA<br>Primer Seq 2 (R) (SEQ ID NO. 11): TCTTCCTCTCCCTTCCCTCCGC | Allele 1 Probe (PF1) (SEQ ID NO. 12): CGCGAcTCTCCTC<br>Allele 2 Probe (PV1) (SEQ ID NO. 13): CGCGagTCTCCTC |
| P5467-1 LG-N | Primer Seq 1 (SEQ ID NO. 14): TCCAGGTTAGATTTCTGAACGAAGA<br>Primer Seq 2 (SEQ ID NO. 15): CATCAGCACAAAGGGCATCCTCA | Allele 1 Probe (SEQ ID NO. 16): CACTCCTTAAGtAAT<br>Allele 2 Probe (SEQ ID NO. 17): CACTCCTTAAGaTAAT |

FIG. 4

MOLECULAR MARKERS LINKED TO PPO INHIBITOR TOLERANCE IN SOYBEANS

CROSS-REFERENCE TO RELATED APPLICATIONS

This application claims priority under 35 U.S.C. §119(e) to provisional application Ser. No. 61/083,038 filed Jul. 23, 2008, herein incorporated by reference in its entirety.

FIELD OF THE INVENTION

This invention relates generally to the detection of genetic differences among soybeans.

BACKGROUND OF THE INVENTION

Soybeans (*Glycine max* L. Merr.) are a major cash crop and investment commodity in North America and elsewhere. Soybean oil is one of the most widely used edible oils, and soybeans are used worldwide both in animal feed and in human food production. Additionally, soybean utilization is expanding to industrial, manufacturing, and pharmaceutical applications. Weed management in soybean fields is important to maximizing yields. A recent development in soybean technology has been the development of herbicide-tolerant soybean varieties. Glyphosate tolerant soybeans were commercially introduced in 1996 and accounted for more than 85% percent of U.S. soybean acreage in 2007.

Some weeds are starting to show increased tolerance to glyphosate. This increased tolerance decreases the effectiveness of glyphosate application and results in lower yields for farmers. As a result there is a need in the art for soybean varieties that are tolerant to other herbicide chemistry.

SUMMARY OF THE INVENTION

This invention relates generally to the detection of genetic differences among soybeans. More particularly, the invention relates to soybean quantitative trait loci (QTL) for tolerance to protoporphyrinogen oxidase (PPOase) inhibitors, to soybean plants possessing these QTLs, which map to a novel chromosomal region, and to genetic markers that are indicative of phenotypes associated with protoporphyrinogen oxidase inhibitor tolerance. Methods and compositions for use of these markers in genotyping of soybean and selection are also disclosed.

A novel method is provided for determining the presence or absence in soybean germplasm of a QTL associated with tolerance to protoporphyrinogen oxidase inhibitors. The tolerance trait has been found to be closely linked to a number of molecular markers that map to linkage groups L and N. Soybean plants, seeds, tissue cultures, variants and mutants having tolerance to protoporphyrinogen oxidase inhibitors produced by the foregoing methods are also provided in this invention.

In accordance with the present invention, the QTL associated with tolerance to protoporphyrinogen oxidase inhibitors maps to soybean linkage group L and/or N. These QTL may be mapped by one or more molecular markers. For linkage group L, the markers include SATT495, P10649C-3, SATT182, SATT388, SATT313, SATT613, or markers closely linked thereto. Other markers of linkage group L may also be used to identify the presence or absence of the gene, including other markers above marker SATT613. For linkage group N, the markers include Sat_379, SCT_195, SATT631, S60167-TB, SATT675, SATT624, SATT080, SATT387, or markers closely linked thereto. Other markers of linkage group N may also be used to identify the presence or absence of the gene, including other markers above marker SATT387.

The information disclosed herein regarding the QTL for tolerance to protoporphyrinogen oxidase inhibitors which maps to soybean linkage group L and/or N is used to aid in the selection of breeding plants, lines and populations containing tolerance to protoporphyrinogen oxidase inhibitors for use in introgression of this trait into elite soybean germplasm, or germplasm of proven genetic superiority suitable for variety release.

Also provided is a method for introgressing a soybean QTL associated with tolerance to protoporphyrinogen oxidase inhibitors into non-tolerant soybean germplasm or less tolerant soybean germplasm. According to the method, nucleic acid markers mapping the QTL are used to select soybean plants containing the QTL. Plants so selected have a high probability of expressing the trait tolerance to protoporphyrinogen oxidase inhibitors. Plants so selected can be used in a soybean breeding program. Through the process of introgression, the QTL associated with tolerance to protoporphyrinogen oxidase inhibitors is introduced from plants identified using marker-assisted selection to other plants. According to the method, agronomically desirable plants and seeds can be produced containing the QTL associated with tolerance to protoporphyrinogen oxidase inhibitors from germplasm containing the QTL. Sources of tolerance to protoporphyrinogen oxidase inhibitors are disclosed below.

Also provided herein is a method for producing a soybean plant adapted for conferring tolerance to protoporphyrinogen oxidase inhibitors. First, donor soybean plants for a parental line containing the tolerance QTL are selected. According to the method, selection can be accomplished via nucleic acid marker-associated selection as explained herein. Selected plant material may represent, among others, an inbred line, a hybrid, a heterogeneous population of soybean plants, or simply an individual plant. According to techniques well known in the art of plant breeding, this donor parental line is crossed with a second parental line. Typically, the second parental line is a high yielding line. This cross produces a segregating plant population composed of genetically heterogeneous plants. Plants of the segregating plant population are screened for the tolerance QTL and are subjected to further breeding. This further breeding may include, among other techniques, additional crosses with other lines, hybrids, back-crossing, or self-crossing. The result is a line of soybean plants that is tolerant to protoporphyrinogen oxidase inhibitors and also has other desirable traits from one or more other soybean lines.

Soybean plants, seeds, tissue cultures, variants and mutants having tolerance to protoporphyrinogen oxidase inhibitors produced by the foregoing methods are also provided in this invention.

BRIEF DESCRIPTION OF THE DRAWINGS

The invention can be more fully understood from the following detailed description and the accompanying drawings and Sequence Listing, which form a part of this application.

FIG. 1 Panel A provides an integrated genetic map of soybean markers on linkage group L, including the marker type (SSR or ASH/SNP). The genetic map positions of the markers are indicated in centiMorgans (cM), typically with position zero being the first (most distal) marker on the chromosome. Panel B provides a table listing genetic markers that are linked to the protoporphyrinogen oxidase (PPOase)

inhibitor tolerance markers identified by the present invention on linkage group L. These markers are from the soybean public composite map of Jun. 18, 2008 for linkage group L.

FIG. 2 Panel A provides an integrated genetic map of soybean markers on linkage group N, including the marker type (SSR or ASH/SNP). The genetic map positions of the markers are indicated in centiMorgans (cM), typically with position zero being the first (most distal) marker on the chromosome. Panel B provides a table listing genetic markers that are linked to the protoporphyrinogen oxidase (PPOase) inhibitor tolerance markers identified by the present invention on linkage group N. These markers are from the soybean public composite map of Jun. 18, 2008 for linkage group N.

FIG. 3 provides a table listing SSR markers, including those markers that demonstrated linkage disequilibrium with the protoporphyrinogen oxidase (PPOase) inhibitor tolerance phenotype. The table provides the sequences of the left and right PCR primers used in the SSR marker locus genotyping analysis. Also shown is the pigtail sequence used on the 5' end of the right primer.

FIG. 4 provides a table listing the SNP markers that demonstrated linkage disequilibrium with the protoporphyrinogen oxidase (PPOase) inhibitor tolerance phenotype. The table provides the sequences of the PCR primers used to generate a SNP-containing amplicon, and the allele-specific probes that were used to identify the SNP allele in an allele-specific hybridization assay (ASH assay).

Figure 5:

FIG. 5 provides an example of cultivars with vastly different protoporphyrinogen oxidase (PPOase) inhibitor tolerance phenotypes. Shown are field samples, with a non-tolerant variety on the left (white circle: stunted, necrotic) and tolerant variety on the right (normal growth)

Figure 6:
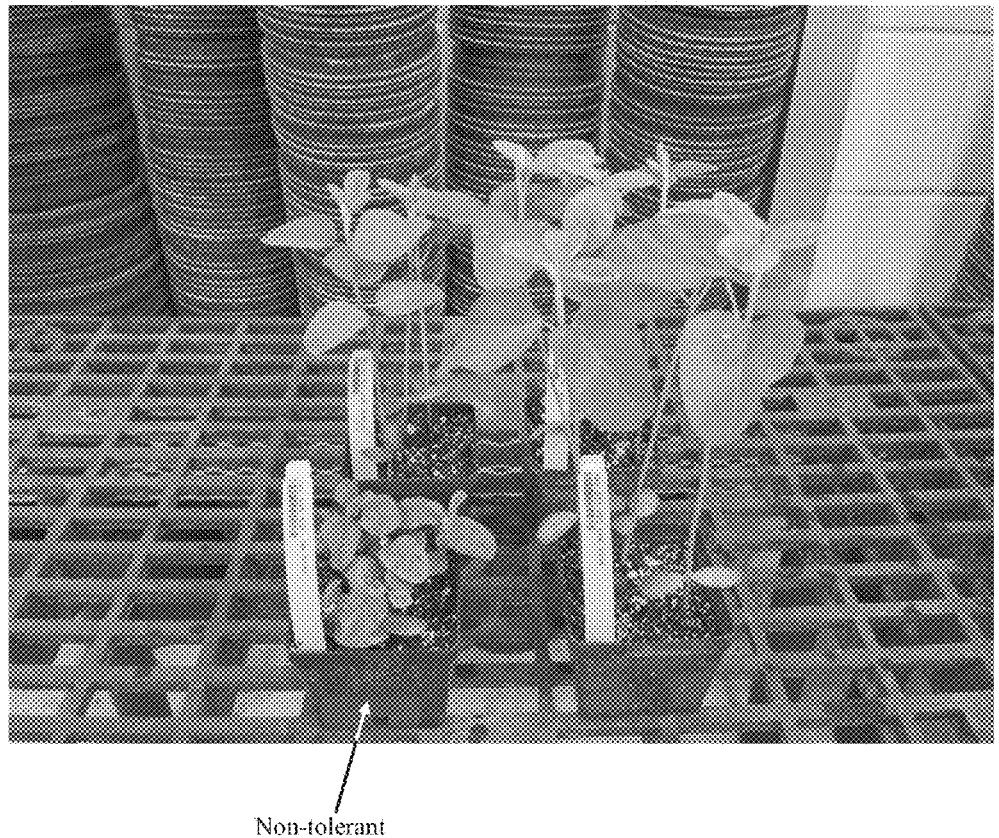

FIG. 6 provides an example of cultivars with vastly different protoporphyrinogen oxidase (PPOase) inhibitor tolerance phenotypes. Shown are greenhouse samples, with a non-tolerant variety with non-tolerant (arrow, left side) and tolerant (right side) variety checks, showing treated plants in the foreground, and untreated plants in the background.

DETAILED DESCRIPTION

It is to be understood that this invention is not limited to particular embodiments or examples, which can, of course, vary. It is also to be understood that the terminology used herein is for the purpose of describing particular embodiments only, and is not intended to be limiting. As used in this specification and the appended claims, terms in the singular and the singular forms "a," "an" and "the," for example, include plural referents unless the content clearly dictates otherwise. Thus, for example, reference to "plant," "the plant" or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules.

Certain definitions used in the specification are provided below. Also in the examples which follow, a number of terms are used. Terms not specifically defined herein should be given their ordinary meaning to those in the art. In order to provide a clear and consistent understanding of the specification and claims, including the scope to be given such terms, the following definitions are provided:

AGRONOMICS, AGRONOMIC TRAITS, and AGRONOMIC PERFORMANCE refer to the traits and underlying genetic elements of a given plant variety that contribute to yield over the course of growing season. Individual agronomic traits include emergence vigor, vegetative vigor, stress tolerance, disease resistance or tolerance, herbicide resistance or tolerance, branching, flowering, seed set, seed size, seed density, standability, threshability and the like.

ALLELE means any of one or more alternative forms of a genetic sequence. In a diploid cell or organism, the two alleles of a given sequence typically occupy corresponding loci on a pair of homologous chromosomes.

The term AMPLIFYING in the context of nucleic acid amplification is any process whereby additional copies of a selected nucleic acid (or a transcribed form thereof) are produced. Typical amplification methods include various polymerase based replication methods, including the polymerase chain reaction (PCR), ligase mediated methods such as the ligase chain reaction (LCR) and RNA polymerase based amplification (e.g., by transcription) methods. An "amplicon" is an amplified nucleic acid, e.g., a nucleic acid that is produced by amplifying a template nucleic acid by any available amplification method (e.g. PCR, LCR, transcription, or the like).

An ANCESTRAL LINE is a parent line used as a source of genes.

An ANCESTRAL POPULATION is a group of ancestors that have contributed the bulk of the genetic variation that was used to develop elite lines.

BACKCROSSING is a process in which a breeder crosses a progeny variety back to one of the parental genotypes one or more times.

BREEDING means the genetic manipulation of living organisms.

The term CHROMOSOME SEGMENT designates a contiguous linear span of genomic DNA that resides in planta on a single chromosome.

CULTIVAR and VARIETY are used synonymously and mean a group of plants within a species (e.g. *Glycine max*) that share certain genetic traits that separate them from the typical form and from other possible varieties within that species. Soybean cultivars are inbred lines produced after several generations of self-pollinations. Individuals within a soybean cultivar are homogeneous, nearly genetically identical, with most loci in the homozygous state.

An ELITE LINE is an agronomically superior line that has resulted from many cycles of breeding and selection for superior agronomic performance. Numerous elite lines are available and known to those of skill in the art of soybean breeding.

An ELITE POPULATION is an assortment of elite individuals or lines that can be used to represent the state of the art in terms of agronomically superior genotypes of a given crop species, such as soybean.

A GENETIC MAP is a description of genetic linkage relationships among loci on one or more chromosomes or linkage groups within a given species, generally depicted in a diagrammatic or tabular form.

GENOTYPE refers to the genetic constitution of a cell or organism.

GERMPLASM means the genetic material that comprises the physical foundation of the hereditary qualities of an organism. As used herein, germplasm includes seeds and living tissue from which new plants may be grown; or, another plant part, such as leaf, stem, pollen, or cells, that may be cultured into a whole plant. Germplasm resources provide sources of genetic traits used by plant breeders to improve commercial cultivars.

An individual is HOMOZYGOUS if the individual has only one type of allele at a given locus (e.g., a diploid individual has a copy of the same allele at a locus for each of two homologous chromosomes). An individual is "HETEROZYGOUS" if more than one allele type is present at a given locus (e.g., a diploid individual with one copy each of two different alleles). The term "HOMOGENEITY" indicates that members of a group have the same genotype at one or more specific loci. In contrast, the term "HETEROGENEITY" is used to indicate that individuals within the group differ in genotype at one or more specific loci.

INTROGRESSION means the entry or introduction of a gene, QTL, or trait locus from the genome of one plant into the genome of another plant.

A LINE or a STRAIN is a group of individuals of identical parentage that are generally inbred to some degree and that are generally homozygous and homogeneous at most loci (isogenic or near isogenic). A "SUBLINE" refers to an inbred subset of descendents that are genetically distinct from other similarly inbred subsets descended from the same progenitor. Traditionally, a subline has been derived by inbreeding the seed from an individual soybean plant selected at the F3 to F5 generation until the residual segregating loci are "fixed" or homozygous across most or all loci. Commercial soybean varieties (or lines) are typically produced by aggregating ("bulking") the self-pollinated progeny of a single F3 to F5 plant from a controlled cross between 2 genetically different parents. While the variety typically appears uniform, the self-pollinating variety derived from the selected plant eventually (e.g. F8) becomes a mixture of homozygous plants that can vary in genotype at any locus that was heterozygous in the originally selected F3 to F5 plant. In the context of the invention, marker-based sublines that differ from each other based on qualitative polymorphism at the DNA level at one or more specific marker loci are derived by genotyping a sample of seed derived from individual self-pollinated progeny derived from a selected F3-F5 plant. The seed sample can be genotyped directly as seed, or as plant tissue grown from such a seed sample. Optionally, seed sharing a common genotype at the specified locus (or loci) are bulked providing a subline that is genetically homogenous at identified loci important for a trait of interest (yield, tolerance, etc.).

LINKAGE refers to a phenomenon wherein alleles on the same chromosome tend to segregate together more often than expected by chance if their transmission was independent. Genetic recombination occurs with an assumed random frequency over the entire genome. Genetic maps are constructed by measuring the frequency of recombination between pairs of traits or markers. The closer the traits or markers lie to each other on the chromosome, the lower the frequency of recombination, and the greater the degree of linkage. Traits or markers are considered herein to be linked if they generally co-segregate. A $\frac{1}{100}$ probability of recombination per generation is defined as a map distance of 1.0 centiMorgan (1.0 cM). For example, in soybean, 1 cM correlates, on average, to about 400,000 base pairs (400 Kb).

The genetic elements or genes located on a single chromosome segment are physically linked. In the context of the present invention the genetic elements located within a chromosome segment are also genetically linked, typically within a genetic recombination distance of less than or equal to 50 centimorgans (cM), e.g. about 49, 40, 30, 20, 10, 5, 4, 3, 2, 1, 0.75, 0.5, or 0.25 cM or less. That is, two genetic elements within a single chromosome segment undergo recombination during meiosis with each other at a frequency of less than or equal to about 50%, e.g., about 49%, 40%, 30%, 20%, 10%, 5%, 4%, 3%, 2%, 1%, 0.75%, 0.5%, or 0.25% or less.

LINKAGE GROUP refers to traits or markers that generally co-segregate. A linkage group generally corresponds to a chromosomal region containing genetic material that encodes the traits or markers.

LOCUS is a defined segment of DNA.

A MAP LOCATION is an assigned location on a genetic map relative to linked genetic markers where a specified marker can be found within a given species. Markers are frequently described as being "above" or "below" other markers on the same linkage group; a marker is "above" another marker if it appears earlier on the linkage group, whereas a marker is "below" another marker if it appears later on the linkage group.

MAPPING is the process of defining the linkage relationships of loci through the use of genetic markers, populations segregating for the markers, and standard genetic principles of recombination frequency.

MOLECULAR MARKER is a nucleic acid or amino acid sequence that is sufficiently unique to characterize a specific locus on the genome. Examples include Restriction Fragment Length Polymorphisms (RFLPs), Single Sequence Repeats (SSRs), Target Region Amplification Polymorphisms (TRAPs), Isozyme Electrophoresis, Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Single Nucleotide Polymorphisms (SNPs). Additionally, other types of molecular markers are known to the art, and phenotypic traits may also be used as markers in the methods of this invention. All markers are used to define a specific locus on the soybean genome. Large numbers of these markers have been mapped. Each marker is therefore an indicator of a specific segment of DNA, having a unique nucleotide sequence. The map positions provide a measure of the relative positions of particular markers with respect to one another. When a trait is stated to be linked to a given marker it will be understood that the actual DNA segment whose sequence affects the trait generally co-segregates with the marker. More precise and definite localization of a trait can be obtained if markers are identified on both sides of the trait. By measuring the appearance of the marker(s) in progeny of crosses, the existence of the trait can be detected by relatively simple molecular tests without actually evaluating the appearance of the trait itself, which can be difficult and time-consuming because the actual evaluation of the trait requires growing plants to a stage where the trait can be expressed. Molecular markers have been widely used to determine genetic composition in soybeans. Shoemaker and Olsen, ((1993) Molecular Linkage Map of Soybean (*Glycine max* L. Merr.). p. 6.131-6.138. In S. J. O'Brien (ed.) Genetic Maps: Locus Maps of Complex Genomes. Cold Spring Harbor Laboratory Press. Cold Spring Harbor, N.Y.), developed a molecular genetic linkage map that consisted of 25 linkage groups with about 365 RFLP, 11 RAPD (random amplified polymorphic DNA), three classical markers, and four isozyme loci. See also Shoemaker R.C. 1994 RFLP Map of Soybean. P. 299-309 In R. L. Phillips and I. K. Vasil (ed.) DNA-based markers in plants. Kluwer Academic Press Dordrecht, the Netherlands.

MARKER ASSISTED SELECTION refers to the process of selecting a desired trait or desired traits in a plant or plants by detecting one or more molecular markers from the plant, where the molecular marker is linked to the desired trait.

The term PHYSICALLY LINKED is used to indicate that two loci, e.g., two marker loci, are physically present on the same chromosome. Advantageously, the two loci are located in close proximity such that recombination between homologous chromosome pairs does not occur between the two loci during meiosis with high frequency, e.g., such that linked loci co-segregate at least about 90% of the time, e.g. 91%, 92%, 93%, 94%, 95%, 96%, 97%, 98%, 99%, 99.5%, 99.75%, or more of the time.

The term PLANT includes reference to an immature or mature whole plant, including a plant from which seed or grain or anthers have been removed. Seed or embryo that will produce the plant is also considered to be the plant.

PLANT PARTS include leaves, stems, buds, roots, root tips, anthers, seed, grain, embryo, pollen, ovules, flowers, cotyledons, hypocotyls, pods, flowers, shoots and stalks, tissues, cells and the like.

POLYMORPHISM means a change or difference between two related nucleic acids. A "NUCLEOTIDE POLYMORPHISM" refers to a nucleotide that is different in one sequence when compared to a related sequence when the two nucleic acids are aligned for maximal correspondence. A "GENETIC NUCLEOTIDE POLYMORPHISM" refers to a nucleotide that is different in one sequence when compared to a related sequence when the two nucleic acids are aligned for maximal correspondence, where the two nucleic acids are genetically related, i.e., homologous, for example, where the nucleic acids are isolated from different strains of a soybean plant, or from different alleles of a single strain, or the like.

PROBE means a polynucleotide designed to be sufficiently complementary to a sequence in a denatured nucleic acid to be probed and to be bound under selected stringency conditions.

RAPD marker means random amplified polymorphic DNA marker. Chance pairs of sites complementary to single octa- or decanucleotides may exist in the correct orientation and close enough to one another for PCR amplification. With some randomly chosen decanucleotides no sequences are amplified. With others, the same length products are generated from DNAs of different individuals. With still others, patterns of bands are not the same for every individual in a population. The variable bands are commonly called random amplified polymorphic DNA (RAPD) bands.

RECOMBINATION FREQUENCY is the frequency of a crossing over event (recombination) between two genetic loci. Recombination frequency can be observed by following the segregation of markers and/or traits during meiosis. In the context of this invention, a marker locus is "associated with" another marker locus or some other locus (for example, a tolerance locus), when the relevant loci are part of the same linkage group and are in linkage disequilibrium. This occurs when the marker locus and a linked locus are found together in progeny plants more frequently than if the two loci segregate randomly. Similarly, a marker locus can also be associated with a trait, e.g., a marker locus can be "associated with tolerance or improved tolerance" when the marker locus is in linkage disequilibrium with the trait.

RFLP means restriction fragment length polymorphism. Molecular markers that occur because any sequence change in DNA, including a single base change, insertion, deletion or inversion, can result in loss or gain of a restriction endonuclease recognition site. The size and number of fragments generated by one such enzyme is therefore altered. A probe that hybridizes specifically to DNA in the region of such an alteration can be used to rapidly and specifically identify a region of DNA that displays allelic variation between two plant varieties. Isozyme Electrophoresis and RFLPs have been widely used to determine genetic composition SELF CROSSING or SELF-POLLINATION or SELFING is a process through which a breeder crosses hybrid progeny with itself; for example, a second generation hybrid F2 with itself to yield progeny designated F2:3.

SNP means single nucleotide polymorphism. SNPs are genetic markers in which DNA sequence variations that occur when a single nucleotide (A, T, C, or G) in the genome sequence is altered are mapped to sites on the soybean genome. Many techniques for detecting SNPs are known in the art, including allele specific hybridization, primer extension, and direct sequencing.

SSR means short sequence repeats. SSRs are genetic markers based on polymorphisms in repeated nucleotide sequences, such as microsatellites. A marker system based on SSRs can be highly informative in linkage analysis relative to other marker systems in that multiple alleles may be present. The PCR detection is done by use of two oligonucleotide primers flanking the polymorphic segment of repetitive DNA. Repeated cycles of heat denaturation of the DNA followed by annealing of the primers to their complementary sequences at low temperatures, and extension of the annealed primers with DNA polymerase, comprise the major part of the methodology.

TOLERANT and TOLERANCE refer to plants in which higher doses of a herbicide are required to produce effects similar to those seen in non-tolerant plants. Tolerant plants typically exhibit fewer necrotic, lytic, chlorotic, or other lesions when subjected to the herbicide at concentrations and rates typically employed by the agricultural community.

TRANSGENIC PLANT refers to a plant that comprises within its cells a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. TRANSGENIC is used herein to refer to any cell, cell line, callus, tissue, plant part or plant, the genotype of which has been altered by the presence of heterologous nucleic acid including those transgenic organisms or cells initially so altered, as well as those created by crosses or asexual propagation from the initial transgenic organism or cell. The term "transgenic" as used herein does not encompass the alteration of the genome (chromosomal or extra-chromosomal) by conventional plant breeding methods (e.g. crosses) or by naturally occurring events such as random cross-fertilization, non-recombinant viral infection, non-recombinant bacterial transformation, non-recombinant transposition, or spontaneous mutation.

TRAP marker means target region amplification polymorphism marker. The TRAP technique employs one fixed primer of known sequence in combination with a random primer to amplify genomic fragments. The differences in fragments between alleles can be detected by gel electrophoresis.

The term VECTOR is used in reference to polynucleotide or other molecules that transfer nucleic acid segment(s) into a cell. The term "vehicle" is sometimes used interchangeably with "vector. " A vector optionally comprises parts which mediate vector maintenance and enable its intended use (e.g. sequences necessary for replication, genes imparting drug or antibiotic resistance, a multiple cloning site, operably linked promoter/enhancer elements which enable the expression of a cloned gene, etc.). Vectors are often derived from plasmids, bacteriophages, or plant or animal viruses. A "cloning vector" or "shuttle vector" or "subcloning vector" contains operably linked parts that facilitate subcloning steps (e.g., a multiple cloning site containing multiple restriction endonuclease sites).

The term YIELD refers to the productivity per unit area of a particular plant product of commercial value. For example, yield of soybean is commonly measured in bushels of seed per acre or metric tons of seed per hectare per season. Yield is affected by both genetic and environmental factors. Yield is the final culmination of all agronomic traits.

Protoporphyrinogen Oxidase Inhibitors

Porphyrins are biologically important organic structures that are found in plants attached to chlorophyll and cytochrome pigments. An intermediate in the chlorophyll and cytochrome synthesis pathway is protoporphyrinogen IX which is converted to protoporphyrin IX by protoporphyrinogen oxidase. Inhibition of protoporphyrinogen oxidase prevents this conversion and results in a buildup of protoporphyrinogen IX in the cytoplasm of the plant. The protoporphyrinogen then undergoes non-enzymatic auto-oxidation and becomes protoporphyrin IX. When cytoplasmic protoporphyrin IX is exposed to sunlight, free radicals are formed which results in lipid peroxidation reactions that result in plant death. Protoporphyrinogen oxidase inhibitor chemical families include diphenyl ether, triazolinone, N-phenylphthalimide, pyrimidindione and oxadiazole families. There are other families of chemistries that also belong to this group.

The diphenyl ether family is characterized by two benzene rings linked with an ether bridge and a nitro group bonded to the 4 position. Examples of diphenyl ether protoporphyrinogen oxidase inhibitors include acifluorfen, fomesafen, oxyfluorfen and lactofen. The diphenyl ethers are typically considered to be contact herbicides.

The triazolinone family is characterized by a 5-member ring containing three nitrogen atoms (two of which are adjacent) and two carbon atoms, one of the carbon atoms has a double bond with an oxygen atom and one of the nitrogen atoms is bonded to a benzene ring. Examples of triazolinone protoprophyrinogen oxidase inhibitors include sulfentrazone, carfentrasone, and azafeniden.

The N-phenylphthalimide family is characterized by pthalimide group wherein the nitrogen is bonded to a benzene ring. Examples of N-phenylphthalimide protoporphyrinogen oxidase inhibitors include flumiclorac and flumioxazin.

The oxadiazole family is characterized by a five member ring consisting of two adjacent nitrogen atoms, two carbon atoms, and an oxygen or sulfur atom. Examples of oxadiazole protoporphyrinogen oxidase inhibitors include oxadiazon and fluthiacet.

The various families of protoporphyrinogen oxidase inhibitors provide a wide variety in application options. Sulfentrazone, for example, has a relatively long half-life (approximately 280 days), is known to have residual soil activity and is frequently used as a pre-emergence herbicide. Carfentrazone has a considerably shorter half-life (approximately 4 days) has no residual soil activity, and is used as a contact/post-emergence herbicide. The pyrimidindiones family of PPO herbicides is a rather small class that includes benzfendizone, butagenacil and saflufenacil. This diversity in chemical characteristics combined with protoporphyrinogen oxidase inhibitor tolerance provides farmers with a wide variety of weed management options.

Molecular Markers and Genetic Linkage

Molecular markers have been used to selectively improve soybean crops through the use of marker assisted selection. Any detectible polymorphic trait can be used as a marker so long as it is inherited differentially and exhibits linkage disequilibrium with a phenotypic trait of interest. A number of soybean markers have been mapped and linkage groups created, as described in Cregan, P. B. et al., "An Integrated Genetic Linkage Map of the Soybean Genome" (1999) Crop Science 39:1464-90, and more recently in Choi et al., "A Soybean Transcript Map: Gene Distribution, Haplotype and Single-Nucleotide Polymorphism Analysis" (2007) Genetics 176:685-96. Many soybean markers are publicly available at the USDA affiliated soybase website.

Most plant traits of agronomic importance are polygenic, otherwise known as quantitative, traits. A quantitative trait is controlled by several genes located at various locations, or loci, in the plant's genome. The multiple genes have a cumulative effect which contributes to the continuous range of phenotypes observed in many plant traits. These genes are referred to as quantitative trait loci (QTL). Recombination frequency measures the extent to which a molecular marker is linked with a QTL. Lower recombination frequencies, typically measured in centiMorgans (cM), indicates greater the linkage between the QTL and the molecular marker. The extent to which two features are linked is often referred to as the genetic distance. The genetic distance is also typically related to the physical distance between the marker and the QTL, however, certain biological phenomenon (including recombinational "hot spots") can affect the relationship between physical distance and genetic distance. Generally, the usefulness of a molecular marker is determined by the genetic and physical distance between the marker and the selectable trait of interest.

The method for determining the presence or absence of a QTL associated with tolerance to protoporphyrinogen oxidase inhibitors in soybean germplasm, comprises analyzing genomic DNA from a soybean germplasm for the presence of at least one molecular marker, wherein at least one molecular marker is linked to the QTL, and wherein the QTL maps to soybean major linkage group L and N and is associated with tolerance to protoporphyrinogen oxidase inhibitors. The term "is associated with" in this context means that the QTL associated with tolerance to protoporphyrinogen oxidase inhibitors has been found, using marker-assisted analysis, to be present in soybean plants showing tolerance to protoporphyrinogen oxidase inhibitors in live bioassays as described herein.

Generally, markers that map closer to the QTL mapped to linkage group L and N and associated with tolerance to protoporphyrinogen oxidase inhibitors are superior to markers that map further from the QTL for use in this invention. In some examples a marker used to determine the presence or absence of a QTL mapping to soybean linkage group L and/or N and associated with tolerance to protoporphyrinogen oxidase inhibitors maps to soybean linkage group L are SATT495, P10649C-3, SATT182, SATT388, SATT313, and SATT613 (or other markers above marker SATT613), and those mapped to linkage group N are Sat_379, SCT_195, SATT631, S60167-TB, SATT675, SATT624, SATT080, and SATT387 (or other markers above SATT387). Any marker assigned to soybean linkage group L and/or N and linked to a marker disclosed herein as associated with tolerance to protoporphyrinogen oxidase inhibitors may be used with the invention. Generally, a linked marker is within 50 cM of the referenced marker. Updated information regarding markers assigned to soybean linkage group L and N may be found on the USDA's Soybase website. Further, linkage group L is now formally referred to as chromosome #19 and linkage group N is now formally referred to as chromosome #3.

Markers flanking the QTL associated with tolerance to protoporphyrinogen oxidase inhibitors are used in the marker-assisted selection processes provided. The genomic DNA of soybean germplasm is typically tested for the presence of at least two of the foregoing molecular markers, one marker on each side of the QTL. In some examples a QTL on linkage group L is used. Useful markers on linkage group L include SATT495, P10649C-3, SATT182, SATT388, SATT313, and SATT613, including markers above SATT613. Markers that map close to SATT495, P10649C-3, SATT182, SATT388, SATT313, and SATT613 can also be used. In some examples a QTL on linkage group N is used. Useful markers on linkage group N include Sat_379, SCT_195, SATT631, S60167-TB, SATT675, SATT624, SATT080, and SATT387, including markers above SATT387. Markers that map close to Sat_379, SCT_195, SATT631, S60167-TB, SATT675, SATT624, SATT080, and SATT387 can also be used.

Methods of introgressing protoporphyrinogen oxidase inhibitor tolerance into non-tolerant or less-tolerant soybean germplasm are provided. Any method for introgressing QTLs into soybean plants can be used. In some examples, a first soybean germplasm that contains tolerance to protoporphyrinogen oxidase inhibitors derived from the QTL mapped to linkage group L and/or N which is associated with tolerance to protoporphyrinogen oxidase inhibitors and a second soybean germplasm that lacks tolerance to protoporphyrinogen oxidase inhibitors derived from the QTL mapped to linkage group L and/or N are provided. The first soybean plant may be crossed with the second soybean plant to provide progeny soybeans. Phenotypic and/or marker screening is then performed on the progeny plants to determine the presence of tolerance to protoporphyrinogen oxidase inhibitors derived from the QTL mapped to linkage group L and/or N. Progeny that test positive for the presence of tolerance to protoporphyrinogen oxidase inhibitors derived from the QTL mapped to linkage group L and/or N can be selected.

In some examples, the screening and selection are performed by using marker-assisted selection using any marker or combination of markers on major linkage group L and/or N provided. Any method of identifying the presence or absence of these markers may be used, including for example single-strand conformation polymorphism (SSCP) analysis, base excision sequence scanning (BESS), RFLP analysis, heteroduplex analysis, denaturing gradient gel electrophoresis, and temperature gradient electrophoresis, allelic PCR, ligase chain reaction direct sequencing, mini sequencing, nucleic acid hybridization, or micro-array-type detection.

Systems, including automated systems for selecting plants that comprise a marker of interest and/or for correlating presence of the marker with tolerance are also provided. These systems can include probes relevant to marker locus detection, detectors for detecting labels on the probes, appropriate fluid handling elements and temperature controllers that mix probes and templates and/or amplify templates, and systems instructions that correlate label detection to the presence of a particular marker locus or allele.

Kits are also provided. For example, a kit can include appropriate primers or probes for detecting tolerance associated marker loci and instructions in using the primers or probes for detecting the marker loci and correlating the loci with predicted protoporphyrinogen oxidase inhibitor tolerance. The kits can further include packaging materials for packaging the probes, primers or instructions, controls such as control amplification reactions that include probes, primers or template nucleic acids for amplifications, molecular size markers, or the like.

Isolated nucleic acid fragments comprising a nucleic acid sequence coding for soybean tolerance to protoporphyrinogen oxidase inhibitors, are provided. The nucleic acid fragment comprises at least a portion of nucleic acid belonging to linkage group L and/or N. The nucleic acid fragment is capable of hybridizing under stringent conditions to nucleic acid of a soybean cultivar tolerant to protoporphyrinogen oxidase inhibitors containing a QTL associated with protoporphyrinogen oxidase inhibitor tolerance that is located on major linkage group L and/or N.

Vectors comprising such nucleic acid fragments, expression products of such vectors expressed in a host compatible therewith, antibodies to the expression product (both polyclonal and monoclonal), and antisense nucleic acid to the nucleic acid fragment are also provided.

Seed of a soybean produced by crossing a soybean variety having protoporphyrinogen oxidase inhibitor tolerance QTL located on major linkage group L and/or N in its genome with another soybean variety, and progeny thereof, are provided.

Tolerance Markers and Favorable Alleles

In traditional linkage analysis, no direct knowledge of the physical relationship of genes on a chromosome is required. Mendel's first law is that factors of pairs of characteristics are segregated, meaning that alleles of a diploid trait separate into two gametes and then into different offspring. Classical linkage analysis can be thought of as a statistical description of the relative frequencies of cosegregation of different traits. Linkage analysis, as described previously, is the well-characterized descriptive framework of how traits are grouped together based upon the frequency with which they segregate together. Because chromosomal distance is approximately proportional to the frequency of crossing over events between traits, there is an approximate physical distance that correlates with recombination frequency.

Marker loci are traits, and can be assessed according to standard linkage analysis by tracking the marker loci during segregation. Thus, one cM is equal to a 1% chance that a marker locus will be separated from another locus (which can be any other trait, e.g., another marker locus, or another trait locus that encodes a QTL), due to crossing over in a single generation. The markers herein, e.g., for linkage group L: SATT495, P10649C-3, SATT182, SATT388, SATT313, and SATT613 (and other markers above SATT613) and for linkage group N: Sat_379, SCT_195, SATT631, S60167-TB, SATT675, SATT624, SATT080, and SATT387 (and other markers above SATT387), have been found to correlate with tolerance or improved tolerance to protoporphyrinogen oxidase inhibitors in soybean. This means that the markers are sufficiently proximal to a tolerance trait that they can be used as a predictor for the tolerance trait itself, using, for example, marker assisted selection (MAS). Soybean plants or germplasm can be selected for markers or marker alleles that positively correlate with tolerance, without actually raising soybean and measuring for tolerance or improved tolerance (or, contrawise, soybean plants can be selected against if they possess markers that negatively correlate with tolerance or improved tolerance. MAS is a powerful shortcut to selecting for desired phenotypes and for introgressing desired traits into cultivars of soybean (e.g., introgressing desired traits into elite lines). MAS is easily adapted to high throughput molecular analysis methods that can quickly screen large numbers of plant or germplasm genetic material for the markers of interest and is much more cost effective than raising and observing plants for visible traits.

Any marker that is linked to a trait of interest (e.g., in the present case, a tolerance or improved tolerance trait) can be used as a marker for that trait. Thus, in addition to the markers described herein, markers linked to the markers itemized herein can also be used to predict the tolerance or improved tolerance trait. Such linked markers are particularly useful when they are sufficiently proximal to a given marker so that they display a low recombination frequency with the given marker. Markers closely linked to the markers on linkage group L and/or linkage group N are also provided. Closely linked markers display a cross over frequency with a given marker of about 10% or less (the given marker is within 10 cM of the given marker). Put another way, closely linked loci co-segregate at least 90% of the time.

Marker loci are especially useful when they are closely linked to target loci (e.g., QTL for tolerance, or, alternatively, simply other marker loci, such as those identified herein, that are linked to such QTL) for which they are being used as markers. A marker more closely linked to a target locus is a better indicator for the target locus (due to the reduced cross-over frequency between the target locus and the marker). Thus, in one example, closely linked loci such as a marker locus and a second locus (e.g., a given marker or a QTL) display an inter-locus cross-over frequency of about 10% or less, about 9% or less, about 8% or less, about 7% or less, about 6% or less, about 5% or less, about 4% or less, about 3% or less, or about 2% or less. In some examples, the relevant loci (e.g., a marker locus and a target locus such as a QTL) display a recombination a frequency of about 1% or less, e.g., about 0.75% or less, about 0.5% or less, or about 0.25% or less. Thus, the loci are about 10 cM, 9 cM, 8 cM, 7 cM, 6 cM, 5 cM, 4 cM, 3 cM, 2 cM, 1 cM, 0.75 cM, 0.5 cM or 0.25 cM or less apart. Put another way, two loci that are localized to the same chromosome, and at such a distance that recombination between the two loci occurs at a frequency of no more than 10% (e.g. about 9%, 8%, 7%, 6%, 5%, 4%, 3%, 2%, 1%, 0.75%, 0.5%, 0.25%, or less) are said to be proximal to each other.

When referring to the relationship between two genetic elements, such as a genetic element contributing to tolerance and a proximal marker, "coupling" phase linkage indicates the state where the "favorable" allele at the tolerance locus is physically associated on the same chromosome strand as the "favorable" allele of the respective linked marker locus. In coupling phase, both favorable alleles are inherited together by progeny that inherit that chromosome strand. In "repulsion" phase linkage, the "favorable" allele at the locus of interest (e.g. a QTL for tolerance) is physically linked with an "unfavorable" allele at the proximal marker locus, and the two "favorable" alleles are not inherited together (i.e., the two loci are "out of phase" with each other).

Optionally, one, two, three or more favorable allele(s) are identified in, or introgressed into the plant. Many marker alleles can be selected for or against during MAS. Plants or germplasm are identified that have at least one such favorable allele that positively correlates with tolerance or improved tolerance. However, it is useful for exclusionary purposes during breeding to identify alleles that negatively correlate with tolerance, to eliminate such plants or germplasm from subsequent rounds of breeding.

The identification of favorable marker alleles is germplasm-specific. The determination of which marker alleles correlate with tolerance (or non-tolerance) is determined for the particular germplasm under study. One of skill recognizes that methods for identifying the favorable alleles are routine and well known, and furthermore, that the identification and use of such favorable alleles is well within the scope of the invention.

Amplification primers for amplifying marker loci and suitable marker probes to detect marker loci or to genotype SNP alleles are provided. Optionally, other sequences to either side of the given primers can be used in place of the given primers, so long as the primers can amplify a region that includes the allele to be detected. Further, it will be appreciated that the precise probe to be used for detection can vary, e.g., any probe that can identify the region of a marker amplicon to be detected can be substituted for those examples provided herein. The configuration of the amplification primers and detection probes can, of course, vary. Thus, the invention is not limited to the primers and probes specifically recited herein.

In some examples the presence of marker loci is directly detected in unamplified genomic DNA by performing a Southern blot on a sample of genomic DNA using probes to the marker loci. Procedures for performing Southern blotting, amplification (PCR, LCR, or the like) and many other nucleic acid detection methods are well established and are taught, e.g., in Sambrook et al., *Molecular Cloning—A Laboratory Manual* (3d ed.), Vol. 1-3, Cold Spring Harbor Laboratory, Cold Spring Harbor, N.Y., 2000 ("Sambrook"); *Current Protocols in Molecular Biology*, F. M. Ausubel et al., eds., Current Protocols, a joint venture between Greene Publishing Associates, Inc. and John Wiley & Sons, Inc., (supplemented through 2002) ("Ausubel")) and *PCR Protocols A Guide to Methods and Applications* (Innis et al. eds) Academic Press Inc. San Diego, Calif. (1990) (Innis). Additional details regarding detection of nucleic acids in plants can also be found, e.g., in *Plant Molecular Biology* (1993) Croy (ed.) BIOS Scientific Publishers, Inc.

Separate detection probes can also be omitted in amplification/detection methods, e.g., by performing a real time amplification reaction that detects product formation by modification of the relevant amplification primer upon incorporation into a product, incorporation of labeled nucleotides into an amplicon, or by monitoring changes in molecular rotation properties of amplicons as compared to unamplified precursors (e.g., by fluorescence polarization).

Typically, molecular markers are detected by any established method available, including, without limitation, allele specific hybridization (ASH) or other methods for detecting single nucleotide polymorphisms (SNP), amplified fragment length polymorphism (AFLP) detection, amplified variable sequence detection, randomly amplified polymorphic DNA (RAPD) detection, restriction fragment length polymorphism (RFLP) detection, self-sustained sequence replication detection, simple sequence repeat (SSR) detection, single-strand conformation polymorphisms (SSCP) detection, isozyme markers detection, or the like. While the exemplary markers provided in the tables herein are either SSR or SNP (ASH) markers, any of the aforementioned marker types can be employed to identify chromosome segments encompassing genetic element that contribute to superior agronomic performance (e.g., tolerance or improved tolerance).

In another example, the presence or absence of a molecular marker is determined by nucleotide sequencing of the polymorphic marker region. This method is readily adapted to high throughput analysis as are the other methods noted above, e.g., using available high throughput sequencing methods such as sequencing by hybridization.

In general, the majority of genetic markers rely on one or more property of nucleic acids for their detection. For example, some techniques for detecting genetic markers utilize hybridization of a probe nucleic acid to nucleic acids corresponding to the genetic marker (e.g., amplified nucleic acids produced using genomic soybean DNA as a template). Hybridization formats, including but not limited to solution phase, solid phase, mixed phase, or in situ hybridization assays are useful for allele detection. An extensive guide to the hybridization of nucleic acids is found in Tijssen (1993) *Laboratory Techniques in Biochemistry and Molecular Biology—Hybridization with Nucleic Acid Probes* Elsevier, N.Y., as well as in Sambrook, Berger and Ausubel.

For example, markers that comprise restriction fragment length polymorphisms (RFLP) are detected, e.g., by hybridizing a probe which is typically a sub-fragment (or a synthetic oligonucleotide corresponding to a sub-fragment) of the nucleic acid to be detected to restriction digested genomic DNA. The restriction enzyme is selected to provide restriction fragments of at least two alternative (or polymorphic) lengths in different individuals or populations. Determining one or more restriction enzyme that produces informative fragments for each cross is a simple procedure. After separation by length in an appropriate matrix (e.g., agarose, polyacrylamide, etc.) and transfer to a membrane (e.g. nitrocellulose, nylon, etc.), the labeled probe is hybridized under conditions which result in equilibrium binding of the probe to the target followed by removal of excess probe by washing.

Nucleic acid probes to the marker loci can be cloned and/or synthesized. Any suitable label can be used with a probe. Detectable labels suitable for use with nucleic acid probes include, for example, any composition detectable by spectroscopic, radioisotopic, photochemical, biochemical, immunochemical, electrical, optical or chemical means. Useful labels include biotin for staining with labeled streptavidin conjugate, magnetic beads, fluorescent dyes, radiolabels, enzymes, and calorimetric labels. Other labels include ligands, which bind to antibodies labeled with fluorophores, chemiluminescent agents, and enzymes. A probe can also constitute radiolabelled PCR primers that are used to generate a radiolabelled amplicon. Methods and reagents for labeling nucleic acids and corresponding detection strategies can be found, e.g., in Haugland (1996) *Handbook of Fluorescent Probes and Research Chemicals Sixth Edition* by Molecular Probes, Inc. (Eugene Oreg.); or Haugland (2001) *Handbook of Fluorescent Probes and Research Chemicals Eighth Edition* by Molecular Probes, Inc. (Eugene Oreg.).

Amplification-based Detection Methods

PCR, RT-PCR and LCR are in particularly broad use as amplification and amplification-detection methods for amplifying nucleic acids of interest (e.g., those comprising marker loci), facilitating detection of the markers. Details regarding the use of these and other amplification methods can be found in any of a variety of standard texts, including, e.g., Sambrook, Ausubel, Berger and Croy, supra. Many available biology texts also have extended discussions regarding PCR and related amplification methods. Any RNA can be converted into a double stranded DNA suitable for restriction digestion, PCR expansion and sequencing using reverse transcriptase and a polymerase ("Reverse Transcription-PCR, or "RT-PCR"). See also Ausubel, Sambrook and Berger, supra.

Real Time Amplification/Detection Methods

In one aspect, real time PCR or LCR is performed on the amplification mixtures described herein, e.g., using molecular beacons or TaqMan™ probes. A molecular beacon (MB) is an oligonucleotide or peptide nucleic acid (PNA) which, under appropriate hybridization conditions, self-hybridizes to form a stem and loop structure. The MB has a label and a quencher at the termini of the oligonucleotide or PNA; thus, under conditions that permit intra-molecular hybridization, the label is typically quenched (or at least altered in its fluorescence) by the quencher. Under conditions where the MB does not display intra-molecular hybridization (e.g., when bound to a target nucleic acid, e.g., to a region of an amplicon during amplification), the MB label is unquenched and signal is detected. Standard methods of making and using MBs are known and MBs and reagents are commercially available. See also, e.g. Leone et al. (1995) "Molecular beacon probes combined with amplification by NASBA enable homogenous real-time detection of RNA." *Nucleic Acids Res.* 26:2150-2155; Tyagi and Kramer (1996) "Molecular beacons: probes that fluoresce upon hybridization" *Nature Biotechnology* 14:303-308; Blok and Kramer (1997) "Amplifiable hybridization probes containing a molecular switch" *Mol Cell Probes* 11: 187-194; Hsuih et al. (1997) "Novel, ligation-dependent PCR assay for detection of hepatitis C in serum" *J Clin Microbiol* 34:501-507; Kostrikis et al. (1998) "Molecular beacons: spectral genotyping of human alleles" *Science* 279:1228-1229; Sokol et al. (1998) "Real time detection of DNA:RNA hybridization in living cells" *Proc. Natl. Acad. Sci. U.S.A.* 95:11538-11543; Tyagi et al. (1998) "Multicolor molecular beacons for allele discrimination" *Nature Biotechnology* 16:49-53; Bonnet et al. (1999) "Thermodynamic basis of the chemical specificity of structured DNA probes" *Proc. Natl. Acad. Sci. U.S.A.* 96:6171-6176; Fang et al. (1999) "Designing a novel molecular beacon for surface-immobilized DNA hybridization studies" *J. Am. Chem. Soc.* 121: 2921-2922; Marras et al. (1999) "Multiplex detection of single-nucleotide variation using molecular beacons" *Genet. Anal. Biomol. Eng.* 14:151-156; and Vet et al. (1999) "Multiplex detection of four pathogenic retroviruses using molecular beacons" *Proc. Natl. Acad. Sci. U.S.A.* 96:6394-6399. See also, e.g. U.S. Pat. No. 5,925,517 (Jul. 20, 1999) to Tyagi et al. entitled "Detectably labeled dual conformation oligonucleotide probes, assays and kits;" U.S. Pat. No. 6,150, 097 to Tyagi et al. (Nov. 21, 2000) entitled "Nucleic acid detection probes having non-FRET fluorescence quenching and kits and assays including such probes" and U.S. Pat. No. 6,037,130 to Tyagi et al. (Mar. 14, 2000), entitled "Wavelength-shifting probes and primers and their use in assays and kits."

PCR detection and quantification using dual-labeled fluorogenic oligonucleotide probes can be done, using for example TAQMAN® type probes. These probes are composed of short (e.g. 20-25 base) oligodeoxynucleotides that are labeled with two different fluorescent dyes. On the 5' terminus of each probe is a reporter dye, and on the 3' terminus of each probe a quenching dye is found. The oligonucleotide probe sequence is complementary to an internal target sequence present in a PCR amplicon. When the probe is intact, energy transfer occurs between the two fluorophores and emission from the reporter is quenched by the quencher by FRET. During the extension phase of PCR, the probe is cleaved by 5' nuclease activity of the polymerase used in the reaction, thereby releasing the reporter from the oligonucleotide-quencher and producing an increase in reporter emission intensity. Accordingly, TAQMAN® type probes are oligonucleotides that have a label and a quencher, where the label is released during amplification by the exonuclease action of the polymerase used in amplification. This provides a real time measure of amplification during synthesis. A variety of TAQMAN® type reagents are commercially available, e.g., from Applied Biosystems (Division Headquarters in Foster City, Calif.) as well as from a variety of specialty vendors such as Biosearch Technologies (e.g. black hole quencher probes).

Additional Details Regarding Amplified Variable Sequences SSR, AFLP ASH, SNPs and Isozyme Markers Amplified variable sequences refer to amplified sequences of the plant genome, which exhibit high nucleic acid residue variability between members of the same species. All organisms have variable genomic sequences and each organism (with the exception of a clone) has a different set of variable sequences. Once identified, the presence of specific variable sequence can be used to predict phenotypic traits. Typically, DNA from the plant serves as a template for amplification with primers that flank a variable sequence of DNA. The variable sequence is amplified and then sequenced.

Alternatively, self-sustained sequence replication can be used to identify genetic markers. Self-sustained sequence replication refers to a method of nucleic acid amplification using target nucleic acid sequences which are replicated exponentially in vitro under substantially isothermal conditions by using three enzymatic activities involved in retroviral replication: (1) reverse transcriptase, (2) Rnase H, and (3) a DNA-dependent RNA polymerase (Guatelli et al. (1990) *Proc Natl Acad Sci USA* 87:1874). By mimicking the retroviral strategy of RNA replication by means of cDNA intermediates, this reaction accumulates cDNA and RNA copies of the original target.

Amplified fragment length polymophisms (AFLP) can also be used as genetic markers (Vos et al. (1995) *Nucl Acids Res* 23:4407). The phrase "amplified fragment length polymorphism" refers to selected restriction fragments, which are amplified before or after cleavage by a restriction endonuclease. The amplification step allows easier detection of specific restriction fragments. AFLP allows the detection large numbers of polymorphic markers and has been used for genetic mapping of plants (Becker et al. (1995) Mol Gen Genet 249:65; and Meksem et al. (1995) Mol Gen Genet 249:74).

Allele-specific hybridization (ASH) can be used to identify the genetic markers of the invention. ASH technology is based on the stable annealing of a short, single-stranded, oligonucleotide probe to a completely complementary single-strand target nucleic acid. Detection is via an isotopic or non-isotopic label attached to the probe.

For each polymorphism, two or more different ASH probes are designed to have identical DNA sequences except at the polymorphic nucleotides. Each probe will have exact homology with one allele sequence so that the range of probes can distinguish all the known alternative allele sequences. Each probe is hybridized to the target DNA. With appropriate probe design and hybridization conditions, a single-base mismatch between the probe and target DNA will prevent hybridization. In this manner, only one of the alternative probes will hybridize to a target sample that is homozygous or homogenous for an allele. Samples that are heterozygous or heterogeneous for two alleles will hybridize to both of two alternative probes.

ASH markers are used as dominant markers where the presence or absence of only one allele is determined from hybridization or lack of hybridization by only one probe. The alternative allele may be inferred from the lack of hybridization. ASH probe and target molecules are optionally RNA or DNA; the target molecules are any length of nucleotides beyond the sequence that is complementary to the probe; the probe is designed to hybridize with either strand of a DNA target; the probe ranges in size to conform to variously stringent hybridization conditions, etc.

PCR allows the target sequence for ASH to be amplified from low concentrations of nucleic acid in relatively small volumes. Otherwise, the target sequence from genomic DNA is digested with a restriction endonuclease and size separated by gel electrophoresis. Hybridizations typically occur with the target sequence bound to the surface of a membrane or, as described in U.S. Pat. No. 5,468,613, the ASH probe sequence may be bound to a membrane.

In one example, ASH data are typically obtained by amplifying nucleic acid fragments (amplicons) from genomic DNA using PCR, transferring the amplicon target DNA to a membrane in a dot-blot format, hybridizing a labeled oligonucleotide probe to the amplicon target, and observing the hybridization dots by autoradiography.

Single nucleotide polymorphisms (SNP) are markers that consist of a shared sequence differentiated on the basis of a single nucleotide. Typically, this distinction is detected by differential migration patterns of an amplicon comprising the SNP on, e.g., an acrylamide gel. However, alternative modes of detection, such as hybridization, e.g. ASH, or RFLP analysis are also appropriate.

Isozyme markers can be employed as genetic markers, e.g., to track markers other than the tolerance markers herein, or to track isozyme markers linked to the markers herein. Isozymes are multiple forms of enzymes that differ from one another in their amino acid sequence, and therefore their nucleic acid sequences. Some isozymes are multimeric enzymes containing slightly different subunits. Other isozymes are either multimeric or monomeric but have been cleaved from the proenzyme at different sites in the amino acid sequence. Isozymes can be characterized and analyzed at the protein level, or alternatively, isozymes, which differ at the nucleic acid level, can be determined. In such cases any of the nucleic acid based methods described herein can be used to analyze isozyme markers.

Probe/Primer Synthesis Methods

In general, synthetic methods for making oligonucleotides, including probes, primers, molecular beacons, PNAs, LNAs (locked nucleic acids), etc., are well known. For example, oligonucleotides can be synthesized chemically according to the solid phase phosphoramidite triester method described by Beaucage and Caruthers (1981), *Tetrahedron Letts* 22(20): 1859-1862, e.g., using a commercially available automated synthesizer, e.g., as described in Needham-VanDevanter et al. (1984) *Nucleic Acids Res.*, 12:6159-6168. Oligonucleotides, including modified oligonucleotides can also be ordered from a variety of commercial sources known to persons of skill. There are many commercial providers of oligo synthesis services, and thus this is a broadly accessible technology. Any nucleic acid can be custom ordered from any of a variety of commercial sources, such as The Midland Certified Reagent Company (mcrc@oligos.com), The Great American Gene Company (genco.com), ExpressGen Inc. (expressgen.com), Operon Technologies Inc. (Alameda, Calif.) and many others. Similarly, PNAs can be custom ordered from any of a variety of sources, such as PeptidoGenic (pkim@ccnet.com), HTI Bio-products, inc. (htibio.com), BMA Biomedicals Ltd (U.K.), Bio. Synthesis, Inc., and many others.

In Silico Marker Detection

In alternative embodiments, in silico methods can be used to detect the marker loci of interest. For example, the sequence of a nucleic acid comprising the marker locus of interest can be stored in a computer. The desired marker locus sequence or its homolog can be identified using an appropriate nucleic acid search algorithm as provided by, for example, in such readily available programs as BLAST, or even simple word processors.

Amplification Primers for Marker Detection

In some examples, molecular markers are detected using a suitable PCR-based detection method, where the size or sequence of the PCR amplicon is indicative of the absence or presence of the marker (e.g., a particular marker allele). In these types of methods, PCR primers are hybridized to the conserved regions flanking the polymorphic marker region. Suitable primers can be designed using any suitable method. It is not intended that the invention be limited to any particular primer or primer pair. For example, primers can be designed using any suitable software program, such as LASERGENE®.

In some examples, the primers are radiolabelled, or labeled by any suitable means (e.g., using a non-radioactive fluorescent tag), to allow for rapid visualization of the different size amplicons following an amplification reaction without any additional labeling step or visualization step. In some examples, the primers are not labeled, and the amplicons are visualized following their size resolution, e.g., following agarose gel electrophoresis. In some examples, ethidium bromide staining of the PCR amplicons following size resolution allows visualization of the different size amplicons.

The primers used to amplify the marker loci and alleles herein are not limited to amplifying the entire region of the relevant locus. In some examples, marker amplification produces an amplicon at least 20 nucleotides in length, or alternatively, at least 50 nucleotides in length, or alternatively, at least 100 nucleotides in length, or alternatively, at least 200 nucleotides in length, or up to and including the full length of the amplicon.

Marker Assisted Selection and Breeding of Plants

A primary motivation for development of molecular markers in crop species is the potential for increased efficiency in plant breeding through marker assisted selection (MAS). Genetic markers are used to identify plants that contain a desired genotype at one or more loci, and that are expected to transfer the desired genotype, along with a desired phenotype to their progeny. Genetic markers can be used to identify plants that contain a desired genotype at one locus, or at several unlinked or linked loci (e.g., a haplotype), and that would be expected to transfer the desired genotype, along with a desired phenotype to their progeny. Means to identify plants, particularly soybean plants, that are tolerant, or that exhibit improved tolerance to protoporphyrinogen oxidase inhibitors are provided, for example by identifying plants having a specified marker loci e.g., for linkage group L: SATT495, P10649C-3, SATT182, SATT388, SATT313, and SATT613 (and other markers above SATT613) and/or for linkage group N: Sat_379, SCT_195, SATT631, S60167-TB, SATT675, SATT624, SATT080, and SATT387 (and other markers above SATT387). Similarly, by identifying plants lacking the desired marker locus, non-tolerant or less tolerant plants can be identified, and, e.g., eliminated from subsequent crosses. Similarly, these marker loci can be introgressed into any desired genomic background, germplasm, plant, line, variety, etc., as part of an overall MAS breeding program designed to enhance soybean yield.

In general, the application of MAS uses the identification of a population of tolerant plants and genetic mapping of the tolerance trait. Polymorphic loci in the vicinity of the mapped tolerance trait are chosen as potential tolerance markers. Typically, a marker locus closest to the tolerance locus is a preferred marker. Linkage analysis is then used to determine which polymorphic marker allele sequence demonstrates a statistical likelihood of co-segregation with the tolerant phenotype (thus, a "tolerance marker allele"). Following identification of a marker allele for co-segregation with the tolerance allele, it is possible to use this marker for rapid, accurate screening of plant lines for the tolerance allele without the need to grow the plants through their life cycle and await phenotypic evaluations, and furthermore, permits genetic selection for the particular tolerance allele even when the molecular identity of the actual tolerance QTL is anonymous. Tissue samples can be taken, for example, from the first leaf of the plant and screened with the appropriate molecular marker, and within days it is determined which progeny will advance. Linked markers also remove the impact of environmental factors that can often influence phenotypic expression.

After a desired phenotype (e.g., tolerance to protoporphyrinogen oxidase inhibitors) and a polymorphic chromosomal marker locus are determined to cosegregate, the polymorphic marker locus can be used to select for marker alleles that segregate with the desired tolerance phenotype. This general process is typically called marker-assisted selection (MAS). In brief, a nucleic acid corresponding to the marker nucleic acid is detected in a biological sample from a plant to be selected. This detection can take the form of hybridization of a probe nucleic acid to a marker allele or amplicon thereof, e.g., using allele-specific hybridization, Southern analysis, northern analysis, in situ hybridization, hybridization of primers followed by PCR amplification of a region of the marker, or the like. After the presence (or absence) of a particular marker in the biological sample is verified, the plant is selected, e.g., used to make progeny plants by selective breeding.

Soybean plant breeders desire combinations of tolerance loci with genes for high yield and other desirable traits to develop improved soybean varieties. Screening large numbers of samples by non-molecular methods (e.g., trait evaluation in soybean plants) can be expensive, time consuming, and unreliable. Use of the polymorphic markers described herein genetically linked to tolerance loci provide effective methods for selecting tolerant varieties in breeding programs. For example, one advantage of marker-assisted selection over field evaluations for tolerance is that MAS can be done at any time of year, regardless of the growing season. Moreover, environmental effects are largely irrelevant to marker-assisted selection.

When a population is segregating for multiple loci affecting one or multiple traits, e.g., multiple loci involved in tolerance, or multiple loci each involved in tolerance or tolerance to different diseases, the efficiency of MAS compared to phenotypic screening becomes even greater, because all of the loci can be evaluated in the lab together from a single sample of DNA. In the present instance, for linkage group L: SATT495, P10649C-3, SATT182, SATT388, SATT313, and SATT613 (or other markers above SATT613) and for linkage group N: Sat_379, SCT_195, SATT631, S60167-TB, SATT675, SATT624, SATT080, and SATT387 (or other markers above SATT387) markers can be assayed simultaneously or sequentially in a single sample or population of samples.

Another use of MAS in plant breeding is to assist the recovery of the recurrent parent genotype by backcross breeding. Backcross breeding is the process of crossing a progeny back to one of its parents or parent lines. Backcrossing is usually done for the purpose of introgressing one or a few loci from a donor parent (e.g., a parent comprising desirable tolerance marker loci) into an otherwise desirable genetic background from the recurrent parent (e.g., an otherwise high yielding soybean line). The more cycles of backcrossing that are done, the greater the genetic contribution of the recurrent parent to the resulting introgressed variety. This is often necessary, because tolerant plants may be otherwise undesirable, e.g., due to low yield, low fecundity, or the like. In contrast, strains which are the result of intensive breeding programs may have excellent yield, fecundity or the like, merely being deficient in one desired trait such as tolerance to protoporphyrinogen oxidase inhibitors.

The presence and/or absence of a particular genetic marker or allele, e.g., for linkage group L: SATT495, P10649C-3, SATT182, SATT388, SATT313, and SATT613 (including markers above SATT613) and for linkage group N: Sat_379, SCT_195, SATT631, S60167-TB, SATT675, SATT624, SATT080, and SATT387 (including markers above SATT387) in the genome of a plant exhibiting a preferred phenotypic trait is made by any method noted herein. If the nucleic acids from the plant are positive for a desired genetic marker, the plant can be self fertilized to create a true breeding line with the same genotype, or it can be crossed with a plant with the same marker or with other desired characteristics to create a sexually crossed hybrid generation.

Introgression of Favorable Alleles—Efficient Crossing of Tolerance Markers into Other Lines One application of MAS is to use the tolerance or improved tolerance markers to increase the efficiency of an introgression or backcrossing effort aimed at introducing a tolerance QTL into a desired (typically high yielding) background. In marker assisted backcrossing of specific markers (and associated QTL) from a donor source, e.g., to an elite genetic background, one selects among progeny or backcross progeny for the donor trait.

Thus, the markers and methods can be utilized to guide marker assisted selection or breeding of soybean varieties with the desired complement (set) of allelic forms of chromosome segments associated with superior agronomic performance (tolerance, along with any other available markers for yield, disease tolerance, etc.). Any of the disclosed marker alleles can be introduced into a soybean line via introgression, by traditional breeding (or introduced via transformation, or both) to yield a soybean plant with superior agronomic performance. The number of alleles associated with tolerance that can be introduced or be present in a soybean plant of the present invention ranges from 1 to the number of alleles disclosed herein, each integer of which is incorporated herein as if explicitly recited.

Methods of making a progeny soybean plant and these progeny soybean plants having tolerance to PPO inhibitors are provided. These methods comprise crossing a first parent soybean plant with a second soybean plant and growing the female soybean plant under plant growth conditions to yield soybean plant progeny. Such soybean plant progeny can be assayed for alleles associated with tolerance and, thereby, the desired progeny selected. Such progeny plants or seed can be sold commercially for soybean production, used for food, processed to obtain a desired constituent of the soybean, or further utilized in subsequent rounds of breeding. At least one of the first or second soybean plants is a soybean plant comprising at least one of the allelic forms of the markers provided, such that the progeny are capable of inheriting the allele.

Inheritance of the desired tolerance allele can be traced, such as from progenitor or descendant lines in the subject soybean plants pedigree such that the number of generations separating the soybean plants being subject to the methods of the present invention will generally be from 1 to 20, commonly 1 to 5, and typically 1, 2, or 3 generations of separation, and quite often a direct descendant or parent of the soybean plant will be subject to the method (i.e., 1 generation of separation).

Methods for Identifying Protoporphyrinogen Oxidase Inhibitor Tolerant Soybean Plants Experienced plant breeders can recognize tolerant soybean plants in the field, and can select the tolerant individuals or populations for breeding purposes or for propagation. In this context, the plant breeder recognizes tolerant, and non-tolerant soybean plants.

The screening and selection may also be performed by exposing plants containing said progeny germplasm to protoporphyrinogen oxidase inhibitors in an assay and selecting those plants showing tolerance to protoporphyrinogen oxidase inhibitors as containing soybean germplasm into which germplasm having tolerance to protoporphyrinogen oxidase inhibitors derived from the QTL mapped to linkage group L and/or N has been introgressed. The live assay may be any such assay known to the art, e.g., Taylor-Lovell et al. (2001) Weed Tech 15:95-102.

However, plant tolerance is a phenotypic spectrum consisting of extremes of high tolerance to non-tolerance with a continuum of intermediate tolerance phenotypes. Evaluation of these intermediate phenotypes using reproducible assays are of value to scientists who seek to identify genetic loci that impart tolerance, conduct marker assisted selection for tolerant population, and for introgression techniques to breed a tolerance trait into an elite soybean line, for example. Describing the continuum of tolerance can be done using any known scoring system or derivative thereof, including the scoring systems described in Examples 1-4.

Automated Detection/Correlation Systems

In some examples, the methods include an automated system for detecting markers and or correlating the markers with a desired phenotype (e.g., tolerance). Thus, a typical system can include a set of marker probes or primers configured to detect at least one favorable allele of one or more marker locus associated with tolerance or improved tolerance to protoporphyrinogen oxidase inhibitors. These probes or primers are configured to detect the marker alleles noted in the tables and examples herein, e.g., using any available allele detection format, e.g., solid or liquid phase array based detection, microfluidic-based sample detection, etc.

In some examples markers involving linkage group L are used. In some examples a marker closely linked to the marker locus of SATT495, P10649C-3, SATT182, SATT388, SATT313, and SATT613 is used, and the probe set is configured to detect the closely linked marker(s). In some examples, the marker locus is SATT495, P10649C-3, SATT182, SATT388, SATT313, and SATT613 (or another marker above SATT613) and the probe set is configured to detect the locus. Similarly, alleles of SATT495, P10649C-3, SATT182, SATT388, SATT313, and SATT613 can be detected.

In some examples markers involving linkage group N are used. In some examples a marker closely linked to the marker locus of Sat_379, SCT_195, SATT631, S60167-TB, SATT675, SATT624, SATT080, and SATT387 (or another marker above SATT387) is used, and the probe set is configured to detect the closely linked marker(s). In some examples the marker locus is Sat_379, SCT_195, SATT631, S60167-TB, SATT675, SATT624, SATT080, and SATT387 and the probe set is configured to detect the locus. Similarly, alleles of Sat_379, SCT_195, SATT631, S60167-TB, SATT675, SATT624, SATT080, and SATT387 can be detected.

The typical system includes a detector that is configured to detect one or more signal outputs from the set of marker probes or primers, or amplicon thereof, thereby identifying the presence or absence of the allele. A wide variety of signal detection apparatus are available, including photo multiplier tubes, spectrophotometers, CCD arrays, arrays and array scanners, scanning detectors, phototubes and photodiodes, microscope stations, galvo-scans, microfluidic nucleic acid amplification detection appliances and the like. The precise configuration of the detector will depend, in part, on the type of label used to detect the marker allele, as well as the instrumentation that is most conveniently obtained for the user. Detectors that detect fluorescence, phosphorescence, radioactivity, pH, charge, absorbance, luminescence, temperature, magnetism or the like can be used. Typical detector examples include light (e.g., fluorescence) detectors or radioactivity detectors. For example, detection of a light emission (e.g., a fluorescence emission) or other probe label is indicative of the presence or absence of a marker allele. Fluorescent detection is generally used for detection of amplified nucleic acids (however, upstream and/or downstream operations can also be performed on amplicons, which can involve other detection methods). In general, the detector detects one or more label (e.g., light) emission from a probe label, which is indicative of the presence or absence of a marker allele.

The detector(s) optionally monitors one or a plurality of signals from an amplification reaction. For example, the detector can monitor optical signals which correspond to "real time" amplification assay results.

System instructions that correlate the presence or absence of the favorable allele with the predicted tolerance are also a feature of the invention. For example, the instructions can include at least one look-up table that includes a correlation between the presence or absence of the favorable alleles and the predicted tolerance or improved tolerance. The precise form of the instructions can vary depending on the components of the system, e.g., they can be present as system software in one or more integrated unit of the system (e.g., a microprocessor, computer or computer readable medium), or can be present in one or more units (e.g., computers or computer readable media) operably coupled to the detector. As noted, in one typical example, the system instructions include at least one look-up table that includes a correlation between the presence or absence of the favorable alleles and predicted tolerance or improved tolerance. The instructions also typically include instructions providing a user interface with the system, e.g., to permit a user to view results of a sample analysis and to input parameters into the system.

The system typically includes components for storing or transmitting computer readable data representing or designating the alleles detected by the methods of the present invention, e.g., in an automated system. The computer readable media can include cache, main, and storage memory and/or other electronic data storage components (hard drives, floppy drives, storage drives, etc.) for storage of computer code. Data representing alleles detected by the method of the present invention can also be electronically, optically, magnetically o transmitted in a computer data signal embodied in a transmission medium over a network such as an intranet or internet or combinations thereof The system can also or alternatively transmit data via wireless, IR, or other available transmission alternatives.

During operation, the system typically comprises a sample that is to be analyzed, such as a plant tissue, or material isolated from the tissue such as genomic DNA, amplified genomic DNA, cDNA, amplified cDNA, RNA, amplified RNA, or the like.

The phrase "allele detection/correlation system" refers to a system in which data entering a computer corresponds to physical objects or processes external to the computer, e.g., a marker allele, and a process that, within a computer, causes a physical transformation of the input signals to different output signals. In other words, the input data, e.g., amplification of a particular marker allele is transformed to output data, e.g., the identification of the allelic form of a chromosome segment. The process within the computer is a set of instructions, or "program," by which positive amplification or hybridization signals are recognized by the integrated system and attributed to individual samples as a genotype. Additional programs correlate the identity of individual samples with phenotypic values or marker alleles, e.g., statistical methods. In addition there are numerous e.g. C/C++ programs for computing, Delphi and/or Java programs for GUI interfaces, and productivity tools (e.g. Microsoft Excel and/or SigmaPlot) for charting or creating look up tables of relevant allele-trait correlations. Other useful software tools in the context of the integrated systems of the invention include statistical packages such as SAS, Genstat, Matlab, Mathematica, and S-Plus and genetic modeling packages such as QU-GENE. Furthermore, additional programming languages such as visual basic are also suitably employed in the integrated systems.

For example, tolerance marker allele values assigned to a population of progeny descending from crosses between elite lines are recorded in a computer readable medium, thereby establishing a database corresponding tolerance alleles with unique identifiers for members of the population of progeny. Any file or folder, whether custom-made or commercially available (e.g., from Oracle or Sybase) suitable for recording data in a computer readable medium is acceptable as a database in the context of the present invention. Data regarding genotype for one or more molecular markers, e.g. ASH, SSR, RFLP, RAPD, AFLP, SNP, isozyme markers or other markers as described herein, are similarly recorded in a computer accessible database. Optionally, marker data is obtained using an integrated system that automates one or more aspects of the assay (or assays) used to determine marker(s) genotype. In such a system, input data corresponding to genotypes for molecular markers are relayed from a detector, e.g., an array, a scanner, a CCD, or other detection device directly to files in a computer readable medium accessible to the central processing unit. A set of system instructions (typically embodied in one or more programs) encoding the correlations between tolerance and the alleles of the invention is then executed by the computational device to identify correlations between marker alleles and predicted trait phenotypes.

Typically, the system also includes a user input device, such as a keyboard, a mouse, a touchscreen, or the like, for, e.g., selecting files, retrieving data, reviewing tables of maker information, etc., and an output device (e.g., a monitor, a printer, etc.) for viewing or recovering the product of the statistical analysis.

Integrated systems comprising a computer or computer readable medium comprising set of files and/or a database with at least one data set that corresponds to the marker alleles herein are provided. The systems optionally also includes a user interface allowing a user to selectively view one or more of these databases. In addition, standard text manipulation software such as word processing software (e.g. Microsoft Word™ or Corel Wordperfect™) and database or spreadsheet software (e.g., spreadsheet software such as Microsoft Excel™, Corel Quattro Pro™, or database programs such as Microsoft Access™ or Paradox™) can be used in conjunction with a user interface (e.g., a GUI in a standard operating system such as a Windows, Macintosh, Unix or Linux system) to manipulate strings of characters corresponding to the alleles or other features of the database.

The systems optionally include components for sample manipulation, e.g. incorporating robotic devices. For example, a robotic liquid control armature for transferring solutions (e.g., plant cell extracts) from a source to a destination, e.g., from a microtiter plate to an array substrate, is optionally operably linked to the digital computer (or to an additional computer in the integrated system). An input device for entering data to the digital computer to control high throughput liquid transfer by the robotic liquid control armature and, optionally, to control transfer by the armature to the solid support is commonly a feature of the integrated system. Many such automated robotic fluid handling systems are commercially available. For example, a variety of automated systems are available from Caliper Technologies (Hopkinton, Mass.), which utilize various Zymate systems, which typically include, e.g., robotics and fluid handling modules. Similarly, the common ORCA® robot, which is used in a variety of laboratory systems, e.g., for microtiter tray manipulation, is also commercially available, e.g., from Beckman Coulter, Inc. (Fullerton, Calif.). As an alternative to conventional robotics, microfluidic systems for performing fluid handling and detection are now widely available, e.g., from Caliper Technologies Corp. (Hopkinton, Mass.) and Agilent technologies (Palo Alto, Calif.).

Systems for molecular marker analysis can include a digital computer with one or more of high-throughput liquid control software, image analysis software for analyzing data from marker labels, data interpretation software, a robotic liquid control armature for transferring solutions from a source to a destination operably linked to the digital computer, an input device (e.g., a computer keyboard) for entering data to the digital computer to control high throughput liquid transfer by the robotic liquid control armature and, optionally, an image scanner for digitizing label signals from labeled probes hybridized, e.g., to markers on a solid support operably linked to the digital computer. The image scanner interfaces with the image analysis software to provide a measurement of, e.g., nucleic acid probe label intensity upon hybridization to an arrayed sample nucleic acid population (e.g., comprising one or more markers), where the probe label intensity measurement is interpreted by the data interpretation software to show whether, and to what degree, the labeled probe hybridizes to a marker nucleic acid (e.g., an amplified marker allele). The data so derived is then correlated with sample identity, to determine the identity of a plant with a particular genotype(s) for particular markers or alleles, e.g., to facilitate marker assisted selection of soybean plants with favorable allelic forms of chromosome segments involved in agronomic performance (e.g., tolerance or improved tolerance).

Optical images, e.g., hybridization patterns viewed (and, optionally, recorded) by a camera or other recording device (e.g., a photodiode and data storage device) are optionally further processed in any of the embodiments herein, e.g., by digitizing the image and/or storing and analyzing the image on a computer. A variety of commercially available peripheral equipment and software is available for digitizing, storing and analyzing a digitized video or digitized optical image, e.g., using PC (Intel x86 or pentium chip-compatible DOS™ operating system, OS2™ operating system, WINDOWS™ operating system, WINDOWS NT™ operating system or WINDOWS95™ operating system based machines), MACINTOSH™ computers, LINUX operating system computers, or UNIX based (e.g. SUN™ work station) computers.

Also included in this invention are soybean plants produced by any of the foregoing methods.

The present invention is illustrated by the following examples. The foregoing and following description of the present invention and the various embodiments are not intended to be limiting of the invention but rather are illustrative thereof. Hence, it will be understood that the invention is not limited to the specific details of these examples.

EXAMPLES

Example 1

Identification of Sulfentrazone Tolerant and Sensitive Soybean Lines—Herbicide Screening Bioassay and Intergroup Association Marker Based Diagnostic Sulfentrazone is a PPO inhibitor and is the active ingredient in AUTHORITY® herbicide. AUTHORITY® 75DF (FMC Corp., Philadelphia, Pa., USA) is a 75% active ingredient formulation of sulfentrazone containing no other active ingredients.

Part 1: Herbicide Bioassay

One hundred sixteen (116) elite soybean lines were screened for sulfentrazone tolerance using the following protocol. Seed of soybean varieties with adequate seed quality, having greater than 85% warm germination were used.

DESIGN AND REPLICATION: After planting, entries were set up in a randomized complete block design, blocked by replication. Three replications per experiment were used. One or more of well established check variety were included in the experiment, such as available public sector check lines.

| Non-tolerant check: | Pioneer 9692, Asgrow A4715 |
| Tolerant check: | Pioneer 9584, Syngenta S5960 |

Growing conditions were as follows (greenhouse/growth chamber): 16 hr photoperiod @ 85° F. (w/ 75° nighttime set back). Lighting is critical to the success of the screening as stated below.

METHOD OF SCREENING: Four inch plastic pots were filled with a high quality universal potting soil. Entries were planted 1 inch deep at the rate of 5 seeds/pot. A bar-coded plastic stake was used to identify each entry. After planting the pots were allowed to sit in greenhouse overnight to acclimate to soil and improve germination. The following day a sulfentrazone herbicide solution was slowly poured over each pot and allowed to evenly soak through entire soil profile. This ensured that each seed was exposed to an equal amount of sulfentrazone. Pots were placed on aluminum trays and placed in a greenhouse or growth chamber under high intensity light conditions with photosynthetic photon flux density (PPFD) of at least 500 µmol/m/s. Proper lighting conditions were necessary for this screening due to the nature of the PPO inhibitor used. Pots were lightly watered so that herbicide was not leached from the soil profile. After soybean emergence the pots were watered by keeping aluminum trays filled with ¾" of water under each pot.

Herbicide Solution:

A) Mix a stock solution of 0.926 g AUTHORITY® 75DF (FMC Corp.), thoroughly dissolved in 1000 ml of water.
B) Mix 10 ml of STOCK SOLUTION in 1000 ml of water to create final solution.
C) Pour 100 ml of FINAL SOLUTION over each pot.

RECORDING DATA: 10-14 days after treatment, plants were ready to be scored. All scores were based on a comparison to the checks and evaluated as follows:

9=Equivalent or better when compared to the tolerant check
7=Very little damage or response noted.
5=Intermediate response or damage
3=Major damage, including stunting and foliar necrosis
1=Severe damage, including severe stunting and necrosis; equivalent or worse when compared to the non-tolerant check Of the 116 soybean lines screened, 102 showed at least some tolerance to sulfentrazone based herbicides and 11 showed high sensitivity. A reference relevant to this protocol would be: Dayan et al. (1997) 'Soybean (*Glycine max*) cultivar differences in response to sulfentrazone' Weed Science 45:634-641.

Part 2: Intergroup Analysis

An "Intergroup Allele Frequency Distribution" analysis was conducted using GENEFLOW™ version 7.0 software.

An intergroup allele frequency distribution analysis provides a method for finding non-random distributions of alleles between two phenotypic groups.

During processing, a contingency table of allele frequencies was constructed and from this a G-statistic and probability were calculated. The G statistic was adjusted by using the William's correction factor. The probability value was adjusted to take into account the fact that multiple tests are being done (thus, there is some expected rate of false positives). The adjusted probability is proportional to the probability that the observed allele distribution differences between the two classes would occur by chance alone. The lower that probability value, the greater the likelihood that the tolerance phenotype and the marker will co-segregate. A more complete discussion of the derivation of the probability values can be found in the GENEFLOW™ version 7.0 software documentation. See also Sokal and Rolf (1981), *Biometry*: The Principles and Practices of Statistics in Biological Research, 2nd ed., San Francisco, W. H. Freeman and Co.

The underlying logic is that markers with significantly different allele distributions between the tolerant and non-tolerant groups (i.e., non-random distributions) might be associated with the trait and can be used to separate them for purposes of marker assisted selection of soybean lines with previously uncharacterized tolerance or non-tolerance to protoporphyrinogen oxidase inhibitors. The present analysis examined one marker locus at a time and determined if the allele distribution within the tolerant group is significantly different from the allele distribution within the non-tolerant group. A statistically different allele distribution is an indication that the marker is linked to a locus that is associated with tolerance or non-tolerance to protoporphyrinogen oxidase inhibitors. In this analysis, unadjusted probabilities less than one are considered significant (the marker and the phenotype show linkage disequilibrium), and adjusted probabilities less than approximately 0.05 are considered highly significant. Allele classes represented by less than 5 observations across both groups were not included in the statistical analysis. In this analysis, 1043 marker loci had enough observations for analysis.

This analysis compares the plants' phenotypic score with the genotypes at the various loci. This type of intergroup analysis neither generates nor requires any map data. Subsequently, map data (for example, a composite soybean genetic map) is relevant in that multiple significant markers that are also genetically linked can be considered as collaborating evidence that a given chromosomal region is associated with the trait of interest.

Results

Table 1 below provides a table listing the soybean markers that demonstrated linkage disequilibrium with the tolerance to protoporphyrinogen oxidase inhibitor phenotype. There were 1043 markers used in this analysis. Also indicated in that table are the chromosomes on which the markers are located and their approximate map position relative to other known markers, given in cM, with position zero being the first (most distal) marker known at the beginning of the chromosome. These map positions are not absolute, and represent an estimate of map position. The statistical probabilities that the marker allele and tolerance phenotype are segregating independently are reflected in the Adjusted Probability values. Out of 584 loci studied in 38 sensitive and 160 tolerant soybean lines, QTLs on Lg L and on Lg N were highly significant, as shown in the table below.

TABLE 1

Intergroup analysis results for LgL and LgN markers

| Locus | Test | Chrom # | Position | G-value | df | Prob(G) | Adj Prob |
|---|---|---|---|---|---|---|---|
| S00224-1 | GW | L | 12.03 | 89.87 | −1 | 0 | 0 |
| P10649C-3 | ASH | L | 3.6 | 86.01 | −1 | 0 | 0 |
| SATT523 | SSR | L | 32.4 | 24.02 | −1 | 0.000001 | 0.000592 |
| S60167-TB | SSR | N | 26 | 62.35 | −1 | 0 | 0 |
| P5467A-1 | ASH | N | 25 | 16.25 | −1 | 0.000056 | 0.032192 |
| P5467A-2 | ASH | N | 25 | 16.2 | −1 | 0.000057 | 0.032731 |

Table 2 below shows the allele distribution between 101 tolerant lines and 32/33 non-tolerant lines analyzed. Lines exhibiting tolerance are indicated in the first column as "TOL," and lines exhibiting non-tolerance are indicated in the first column as "NON." Marker calls for the P10649C-3 locus and the S60167-TB locus were available for 132 and 63 of the lines respectively.

TABLE 2

Allele distribution

| Phenotype | P10649C-3 allele LG-L | S60167-TB allele LG-N |
|---|---|---|
| TOL | 1 | 1 |
| TOL | 1 | 1 |
| TOL | 1 | |
| TOL | 1 | |
| TOL | 1 | |
| TOL | 1 | 2 |
| TOL | 1 | |
| TOL | 1 | |
| TOL | 1 | 1 |
| TOL | 1 | |
| TOL | 1 | 1 |
| TOL | 1 | |
| TOL | 1 | 1 |
| TOL | 1 | 1 |
| TOL | 1 | 1 |
| TOL | 1 | 1 |
| TOL | 1 | |
| TOL | 1 | 1 |
| TOL | 1 | |
| TOL | 1 | |
| TOL | 1 | 1 |
| TOL | 1 | 1 |
| TOL | 1 | |
| TOL | 1 | 1 |
| TOL | 1 | 1 |
| TOL | 1 | 1 |
| TOL | 1 | 1 |
| TOL | 1 | |
| TOL | 1 | 1 |
| TOL | 1 | 1 |
| TOL | 1 | |
| TOL | 1 | |
| TOL | 1 | 1 |
| TOL | 1 | 1 |
| TOL | 1 | |
| TOL | 1 | 1 |
| TOL | 1 | |
| TOL | 1 | |
| TOL | 1 | 1 |
| TOL | 1 | 1 |
| TOL | 1 | 1 |
| TOL | 1 | |
| TOL | 1 | 1 |
| TOL | 1 | 1 |
| TOL | 1 | |
| TOL | 1 | 1 |

TABLE 2-continued

Allele distribution

| Phenotype | P10649C-3 allele LG-L | S60167-TB allele LG-N |
|---|---|---|
| TOL | 1 | |
| TOL | 1 | |
| TOL | 1 | 1 |
| TOL | 1 | 1 |
| TOL | 1 | |
| TOL | 1 | 1 |
| TOL | 1 | 1 |
| TOL | 1 | 1 |
| TOL | 1 | 1 |
| TOL | 1 | |
| TOL | 1 | 1 |
| TOL | 1 | 1 |
| TOL | 1 | |
| TOL | 1 | |
| TOL | 1 | |
| TOL | 1 | |
| TOL | 1 | |
| TOL | 1 | 1 |
| TOL | 1 | |
| TOL | 1 | 1 |
| TOL | 1 | 1 |
| TOL | 1 | |
| TOL | 1 | |
| TOL | 1 | |
| TOL | 1 | 1 |
| TOL | 1 | |
| TOL | 1 | |
| TOL | 1 | |
| TOL | 1 | 1 |
| TOL | 1 | 1 |
| TOL | 1 | 1 |
| TOL | 1 | |
| TOL | 1 | 1 |
| TOL | 1 | |
| TOL | 1 | |
| TOL | 1 | |
| TOL | 1 | |
| TOL | 1 | |
| TOL | 1 | |
| TOL | 1 | |
| TOL | | |
| TOL | 1 | |
| TOL | 1 | |
| TOL | 2 | 2 |
| TOL | 1 | |
| TOL | 1 | |
| TOL | 1 | |
| NON | 3 | 2 |
| NON | 3 | |
| NON | 1 | 1 |
| NON | 1_2 | 2 |
| NON | 3 | 2 |
| NON | 3 | |
| NON | 1 | 1_2 |
| NON | 3 | 2 |
| NON | 2 | 1_2 |
| NON | 3 | 2 |
| NON | 2 | |
| NON | 2 | 2 |
| NON | 2 | 2 |
| NON | 1 | 1 |
| NON | 2_3 | |
| NON | 3 | 2 |
| NON | 3 | 2 |
| NON | 2_3 | |
| NON | 3 | |
| NON | 3 | |
| NON | 1 | 1 |
| NON | 2 | |
| NON | 3 | |
| NON | 3 | 2 |
| NON | 3 | |
| NON | 2 | 2 |
| NON | 3 | 2 |
| NON | 1_3 | 2 |
| NON | 3 | |
| NON | 2 | |
| NON | 1 | |
| NON | 3 | |

The non-random distribution of alleles between the tolerant and non-tolerant plant groups at the marker loci in Table 2 is good evidence that a QTL influencing tolerance to protoporphyrinogen oxidase inhibitors is linked to these marker loci.

Example 2

Predication and Confirmation of Marker Based Selection for Response to PPO Chemistries in a Set of Diverse Public Soybean Lines Marker haplotype data for a set of 17 diverse public soybean lines was determined for two QTL identified in Example 1 for Linkage Group L molecular markers P10649C-3 (approximate position 3.6) and S00224-1 (approximate position 12.0). The response of these lines to sulfentrazone herbicide was published by Hulting et al. (Soybean (*Glycine max* (L.) Merr.) cultivar tolerance to sulfentrazone. 2001 Science Direct, Vol. 20(8): 679-683). The phenotypic response was reported as a growth reduction index: plant height and visual injury as expressed as a percentage of check plot of each cultivar. Data for the marker haplotype on Linkage Group L and the herbicide bioassay results are presented in Table 3. Use of the molecular diagnostic P10649C-3 (linked QTL on Linkage Group L, approximate position 3.6) for this set of phentoyped soybean lines is 92% predictive of tolerance to sulfentrazone when injury is set at 39% or less GRI and is 100% predictive of non-tolerance to sulfentrazone when injury is set at 40% or higher GRI. Use of the S00224-1 marker (approximate position 12.0) for this set of soybean lines is 88% predictive of tolerance to sulfentrazone when injury is set at 39% or less GRI and is 100% predictive of non-tolerance to sulfentrazone when injury is set at 40% or more GRI.

TABLE 3

Marker haplotype at/near QTL on Linkage Group L for PPO herbicide (sulfentrazone) response and phenotypic measure of crop response, expressed in terms of Growth Reduction Index, for soybean cultivars (italicized items indicate deviations from expected)

| Cultivar | Growth Reduction Index* | Linkage Group L QTLs Position 3.6 P10649C-3 | Position 12.0 S00224-1 |
|---|---|---|---|
| PI88788 | 2 | 1, 1 | 3, 3 |
| Richland | 4 | 1, 1 | 3, 3 |
| Lincoln | 5 | 1, 1 | 3, 3 |

TABLE 3-continued

Marker haplotype at/near QTL on Linkage Group L for PPO herbicide (sulfentrazone) response and phenotypic measure of crop response, expressed in terms of Growth Reduction Index, for soybean cultivars (italicized items indicate deviations from expected)

| Cultivar | Linkage Group L QTLs Position 3.6 P10649C-3 | Position 12.0 S00224-1 |
|---|---|---|
| PI180501 | 8 | 1, 1 | 3, 3 |
| Illini | 8 | 1, 1 | 3, 3 |
| S100 | 8 | 1, 1 | 3, 3 |
| Mukden | 8 | 1, 1 | 3, 3 |
| Arksoy | 10 | 1, 1 | 3, 3 |
| Capital | 10 | 1, 1 | 3, 3 |
| Haberlandt | 10 | *3, 3* | *2, 2* |
| Ralsoy | 13 | 1, 1 | *2, 3* |
| Dunfield | 16 | 1, 1 | 3, 3 |
| Peking | 22 | 1, 1 | 3, 3 |
| Roanoke | 40 | 3, 3 | 2, 2 |
| Ogden | 42 | 3, 3 | 2, 2 |
| Hutcheson | 46 | 3, 3 | 2, 2 |
| Ransom | 52 | 3, 3 | 2, 2 |
| allele call load percent accuracy | | | |
| correct tolerant | (alleles 1) 24/26 = 92% | (allele 3) 23/26 = 88% |
| correct non-tolerant | (allele 3) 8/8 = 100% | (allele 2) = 8/8 = 100% |

*growth reduction index (plant height and visual injury as expressed as a percentage of check plot of each cultivar); Pre-emergence sulfentrazone application of 0.28 kg ai/ha, from Hulting, et al. (supra)

Haplotype data for a set of 15 diverse public soybean lines was determined for two QTL identified in Example 1 for Linkage Group N molecular marker S60167 (approximate position 26.0). The response of these 15 lines to sulfentrazone herbicide was determined and published upon by Hulting et al. (Soybean (*Glycine max* (L.) Merr.) cultivar tolerance to sulfentrazone. 2001 Science Direct, Vol. 20(8): 679-683). The phenotypic response was reported as a growth reduction index: plant height and visual injury as expressed as a percentage of check plot of each cultivar. Data for the marker haplotype on Linkage Group N and the herbicide bioassay results are presented in Table 4. The cultivar Ralsoy is heterozygous for the S60167 marker. Use of the S60167 marker for this set of phentoyped soybean lines is 88% predictive of tolerance to sulfentrazone when injury is set at 39% or less GRI and is 100% predictive of tolerance to sulfentrazone when injury is set at 40% or higher GRI.

TABLE 4

Marker haplotype at/near QTL on Linkage Group N for PPO herbicide (sulfentrazone) response and phenotypic measure of crop response, expressed in terms of Growth Reduction Index, for soybean cultivars (italicized items indicate deviations from expected)

| Cultivar | Growth Reduction Index* | Linkage Group N QTL Position 26 S60167-TB |
|---|---|---|
| PI88788 | 2 | 1, 1 |
| Richland | 4 | 1, 1 |
| Lincoln | 5 | 1, 1 |
| Illini | 8 | 1, 1 |
| S100 | 8 | 1, 1 |
| Mukden | 8 | 1, 1 |
| Arksoy | 10 | 1, 1 |
| Haberlandt | 10 | 1, 1 |
| Ralsoy | 13 | *1, 2* |
| Dunfield | 16 | 1, 1 |
| CNS | 20 | *2, 2* |
| Peking | 22 | 1, 1 |
| Roanoke | 40 | 2, 2 |
| Ogden | 42 | 2, 2 |
| Hutcheson | 46 | 2, 2 |
| allele call load percent accuracy | | |
| correct tolerant | (allele 1) 21/24 = 88% | |
| correct non-tolerant | (allele 2) 6/6 = 100% | |

Example 3

Predication and Confirmation of Marker Based Selection for Response to PPO Chemistries in a Set of Soybean Commercial Lines Haplotype data for a set of 7 commercial soybean lines was determined for two QTL identified in the previous example for Linkage Group L molecular markers P10649C-3 (position 3.6) and S00224-1 (position 12.0). The response of these lines to sulfentrazone herbicide was determined by method used in Example 1. In addition, the same scale was used for scoring such that:

9=Equivalent or better when compared to the tolerant check

7=Very little damage or response noted.

5=Intermediate response or damage

3=Major damage, including stunting and foliar necrosis

1=Severe damage, including severe stunting and necrosis; equivalent or worse when compared to the non-tolerant check Data for the marker haplotype on Linkage Group L and the herbicide bioassay results are presented in Table 5. Use of either/both of these markers for this set of phentoyped soybean lines is 100% predictive of both tolerance (score of a 7 or 9) and non-tolerance (score of a 1 for the non-tolerant check).

TABLE 5

Prediction and confirmation of marker based selection at QTL for linkage group L for response to PPO chemistry (sulfentrazone) in a set of commercial soybean varieties.

| Variety | sulfentrazone injury score | Position 3.6 P10649C-3 | Position 12.0 S00224-1 |
|---|---|---|---|
| 93B41 | 9 | 1, 1 | 3, 3 |
| 93B82 | 9 | 1, 1 | 3, 3 |
| 9281 | 9 | 1, 1 | 3, 3 |
| 9584 | 9 | 1, 1 | 3, 3 |
| 92B52 | 7 | 1, 1 | 3, 3 |
| 92B61 | 7 | 1, 1 | 3, 3 |
| 9692 | 1 | 3, 3 | 2, 2 |

Example 4

Predication and Confirmation of Marker Based Selection for Response to PPO Chemistries (Sulfentrazone) in Ten Lines from a Set of Soybean Lines Phenotyped at the University of Illinois A comparison for the marker predictiveness of PPO response was conducted. The herbicide bioassay experiment used is described in Phytoxic Response and Yield of Soybean (*Glycine max*) Varieties Treated with Sulfentrazone or Flumioxazin (Taylor-Lovell et al., 2001 Weed Technology 15:96-102). Phenotypic data was taken from Table 2 of the publication for those varieties for which in-house marker data was available.

Phenotypic score and haplotype data for a set of 10 soybean lines (1 public and 9 commercial) in the chromosomal regions around the QTL for Linkage group L is presented in Table 6. The phenotypic score was determined as percent injury which is defined as visible injury ratings including stunting, chlorosis, and bronzing symptomology (0=no injury; 100=complete death) with 448 g ai/ha field application. Ratings were taken 12 days after treatment. Use of marker P10649C (linked QTL on Linkage Group L, approximate position 3.6, allele call 1) for this set of phentoyped soybean lines is 100% predictive of tolerance (allele call 1) to sulfentrazone when injury is 21% or less and is 100% predictive of non-tolerance (allele call 2 or 3) to sulfentrazone when injury is 43% or greater. The predictiveness of marker S00224-1 is also 100% accurate for tolerance (allele 3) and non-tolerance (allele 2) for this set of material.

TABLE 6

Marker haplotype at/near QTL on Linkage Group L for PPO herbicide (sulfentrazone) response and phenotypic measure of crop injury

| Variety | sulfentrazone injury score | Position 3.6 P10649C-3 | Position 12.0 S00224-1 |
|---|---|---|---|
| P9584 | 5 | 1, 1 | 3, 3 |
| P9671 | 5 | 1, 1 | 3, 3 |
| P9151 | 8 | 1, 1 | 3, 3 |
| P9306 | 15 | 1, 1 | 3, 3 |
| Elgin | 18 | 1, 1 | 3, 3 |
| P9282 | 19 | 1, 1 | 3, 3 |
| P9352 | 21 | 1, 1 | 3, 3 |
| P9362 | 43 | 2, 2 | 2, 2 |
| 91B01 | 58 | 3, 3 | 2, 2 |

TABLE 6-continued

Marker haplotype at/near QTL on Linkage Group L for PPO herbicide (sulfentrazone) response and phenotypic measure of crop injury

| Variety | | Position 3.6 P10649C-3 | Position 12.0 S00224-1 |
|---|---|---|---|
| P9552 | 61 | 3, 3 | 2, 2 |
| LSD (0.05) | 8 | | |
| | allele call load percent accuracy | | |
| | correct tolerant | (alleles 1 or 2) 14/14 = 100% | (allele 3) 14/14 = 100% |
| | correct non-tolerant | (allele 3) 8/8 = 100% | (allele 2) = 8/8 = 100% |

Example 5

Pictures of Soybean Variety Response (Tolerant and Non-tolerant Check Varieties) to Sulfentrazone Injury in the Field and in the Greenhouse/Growth Chamber Bioassay Known non-tolerant (i.e., Pioneer variety 9692, Asgrow variety A4715) and tolerant (i.e., Pioneer variety 9584, Syngenta variety S5960) germplasm can exhibit severe differences in symptomology when field conditions are conducive to damage and when lab conditions for bioassays are optimized for selection purposes. FIGS. 5 and 6 show these differences in phenotype. FIG. 5 shows a field sample, with a non-tolerant variety on the left (stunted, necrotic) and tolerant variety on the right (normal growth). FIG. 6 shows a greenhouse sample, with non-tolerant (left side) and tolerant (right side) variety checks, treated in the foreground, untreated in the background.

It will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

All publications referred to herein are incorporated by reference herein for the purpose cited to the same extent as if each was specifically and individually indicated to be incorporated by reference herein.

What is claimed is:

1. A method of selecting a soybean plant or germplasm with tolerance or improved tolerance to herbicides that inhibit protoporphyrinogen oxidase function, the method comprising:
   a) detecting in a soybean plant or germplasm at least one allele of a marker locus that is associated with the tolerance or improved tolerance to herbicides that inhibit protoporphyrinogen oxidase function, wherein the one or more marker locus is a marker locus localizing within a chromosome interval defined by and including markers SATT495 and SATT613 on linkage group L;
   b) selecting the soybean plant or germplasm comprising the at least one allele of one or more marker locus
   c) applying the herbicides to the plants selected in step b) and selecting plants that have tolerance or improved tolerance to herbicides that inhibit protoporphyrinogen oxidase function.

2. The method of claim 1, wherein said marker locus is localized to a chromosomal interval defined by and including SATT313 and above on linkage group L.

3. The method of claim 1, wherein said marker locus is localized to a chromosomal interval defined by and including markers SATT495 and SATT313 on linkage group L.

4. The method of claim 1, wherein said marker locus is localized to a chromosomal interval defined by and including markers SATT495 and SATT388 on linkage group L.

5. The method of claim 1, wherein said marker locus is localized to a chromosomal interval defined by and including markers P10649C-3 and SATT182 on linkage group L.

6. The method of claim 1, wherein the herbicide is a member of an herbicide family selected from the group consisting of diphenylethers, N-phenylpthalamides, oxadiazole and triazolinones.

7. The method of claim 6, wherein the herbicide is selected from the group consisting of sulfentrazone, carfentrazone-ethyl, aciflourfen, lactofen, fomesafen, flumioxazin, flumiclorac-pentyl and oxyfluorfen.

8. The method of claim 1, wherein the selection occurs as part of further breeding to improve a soybean variety's tolerance to one or more herbicides that inhibit protoporphyrinogen oxidase function.

9. The method of claim 8, wherein the further breeding is selected from the group consisting of additional crosses with other lines, hybrids, backcrossing, self-crossing, and combinations thereof.

10. A method of screening a soybean to determine the presence or absence of a quantitative trait locus associated with tolerance to herbicides that inhibit protoporphyrinogen oxidase function, the method comprising:
   a. screening the soybean for a nucleic acid that localizes within an interval selected from the group consisting of:
      i) the interval flanked by and including markers SATT495 and SATT613;
      ii) the interval flanked by and including markers SATT495 and SATT313;
      iii) the interval flanked by and including markers SATT495 and SATT388; and
      iv) the interval flanked by and including markers P10649C-3 and SATT182; and
   b. determining whether the soybean comprises said nucleic acid, thereby determining the presence or absence of a quantitative trait locus associated with tolerance to herbicides that inhibit protoporphyrinogen oxidase function.

* * * * *

SEQUENCE LISTING

<160> NUMBER OF SEQ ID NOS: 17

<210> SEQ ID NO 1
<211> LENGTH: 22
<212> TYPE: DNA
<213> ORGANISM: Glycine max
<220> FEATURE:
<221> NAME/KEY: source
<222> LOCATION: (0)...(0)
<223> OTHER INFORMATION: S60167-TB LG-N left primer sequence

<400> SEQUENCE: 1
ttattgaggt gggcaaggtg tg                                              22

<210> SEQ ID NO 2
<211> LENGTH: 23
<212> TYPE: DNA
<213> ORGANISM: Glycine max
<220> FEATURE:
<221> NAME/KEY: source
<222> LOCATION: (0)...(0)
<223> OTHER INFORMATION: S60167-TB LG-N right primer sequence

<400> SEQUENCE: 2
catgaacgtc tggtggttga aca                                          23

<210> SEQ ID NO 3
<211> LENGTH: 27
<212> TYPE: DNA
<213> ORGANISM: Glycine max
<220> FEATURE:
<221> NAME/KEY: source
<222> LOCATION: (0)...(0)
<223> OTHER INFORMATION: SATT523 LG-L left primer sequence

<400> SEQUENCE: 3
gcgatttctt ccttgaagaa ttttctg                                      27

<210> SEQ ID NO 4
<211> LENGTH: 27
<212> TYPE: DNA
<213> ORGANISM: Glycine max
<220> FEATURE:
<221> NAME/KEY: source
<222> LOCATION: (0)...(0)
<223> OTHER INFORMATION: SATT523 LG-L right primer sequence

<400> SEQUENCE: 4 gcgcttttc ggctgttatt tttaact                                       27

<210> SEQ ID NO 5
<211> LENGTH: 30
<212> TYPE: DNA
<213> ORGANISM: Glycine max
<220> FEATURE:
<221> NAME/KEY: source
<222> LOCATION: (0)...(0)
<223> OTHER INFORMATION: P10649C-3 LG-L primer sequence 1

<400> SEQUENCE: 5
gagggctatg ttttcttctc cagatgtgag                                   30

<210> SEQ ID NO 6
<211> LENGTH: 26
<212> TYPE: DNA
<213> ORGANISM: Glycine max
<220> FEATURE:
<221> NAME/KEY: source
<222> LOCATION: (0)...(0)
<223> OTHER INFORMATION: P10649C-3 LG-L primer sequence 2

<400> SEQUENCE: 6
aaggtcggct tggtggttaa aggcag                                       26

<210> SEQ ID NO 7
<211> LENGTH: 13
<212> TYPE: DNA
<213> ORGANISM: Artificial Sequence
<220> FEATURE:
<223> OTHER INFORMATION: P10649C-3 LG-L Allele 1 Probe

<400> SEQUENCE: 7

```
tcatctgtga taa                                                           13

<210> SEQ ID NO 8
<211> LENGTH: 13
<212> TYPE: DNA
<213> ORGANISM: Artificial Sequence
<220> FEATURE:
<223> OTHER INFORMATION: P10649C-3 LG-L Allele 2 Probe

<400> SEQUENCE: 8
tcatgtgtga taa                                                           13

<210> SEQ ID NO 9
<211> LENGTH: 13
<212> TYPE: DNA
<213> ORGANISM: Artificial Sequence
<220> FEATURE:
<223> OTHER INFORMATION: P10649C-3 LG-L Allele 3 Probe

<400> SEQUENCE: 9
tcatctctga taa                                                           13

<210> SEQ ID NO 10
<211> LENGTH: 22
<212> TYPE: DNA
<213> ORGANISM: Glycine max
<220> FEATURE:
<221> NAME/KEY: source
<222> LOCATION: (0)...(0)
<223> OTHER INFORMATION: S00224-1 LG-L primer sequence 1 (forward)

<400> SEQUENCE: 10
ctggacctac ccgggatgaa aa                                                 22

<210> SEQ ID NO 11
<211> LENGTH: 22
<212> TYPE: DNA
<213> ORGANISM: Glycine max
<220> FEATURE:
<221> NAME/KEY: source
<222> LOCATION: (0)...(0)
<223> OTHER INFORMATION: S00224-1 LG-L primer sequence 2 (reverse)

<400> SEQUENCE: 11
tcttcctctc ccttcctctc gc                                                 22

<210> SEQ ID NO 12
<211> LENGTH: 13
<212> TYPE: DNA
<213> ORGANISM: Artificial Sequence
<220> FEATURE:
<223> OTHER INFORMATION: S00224-1 LG-L Allele 1 Probe

<400> SEQUENCE: 12
cgcgactctc ctc                                                           13

<210> SEQ ID NO 13
<211> LENGTH: 13
<212> TYPE: DNA
<213> ORGANISM: Artificial Sequence
<220> FEATURE:
<223> OTHER INFORMATION: S00224-1 LG-L Allele 2 Probe

<400> SEQUENCE: 13
cgcgagtctc ctc                                                           13
```

```
<210> SEQ ID NO 14
<211> LENGTH: 27
<212> TYPE: DNA
<213> ORGANISM: Glycine max
<220> FEATURE:
<221> NAME/KEY: source
<222> LOCATION: (0)...(0)
<223> OTHER INFORMATION: P5467-1  LG-N primer sequence 1

<400> SEQUENCE: 14
tcccaggtta gattttctga acgaaga                                         27

<210> SEQ ID NO 15
<211> LENGTH: 24
<212> TYPE: DNA
<213> ORGANISM: Glycine max
<220> FEATURE:
<221> NAME/KEY: source
<222> LOCATION: (0)...(0)
<223> OTHER INFORMATION: P5467-1  LG-N primer sequence 2

<400> SEQUENCE: 15
catcagcaca aaagggcatc ctca                                            24

<210> SEQ ID NO 16
<211> LENGTH: 16
<212> TYPE: DNA
<213> ORGANISM: Artificial Sequence
<220> FEATURE:
<223> OTHER INFORMATION: P5467-1 LG-NL Allele 1 Probe

<400> SEQUENCE: 16
cactccttaa ggtaat                                                     16

<210> SEQ ID NO 17
<211> LENGTH: 16
<212> TYPE: DNA
<213> ORGANISM: Artificial Sequence
<220> FEATURE:
<223> OTHER INFORMATION: P5467-1 LG-NL Allele 2 Probe

<400> SEQUENCE: 17
cactccttaa gataat                                                     16
```